US012563279B2

(12) United States Patent
Yu et al.

(10) Patent No.: US 12,563,279 B2
(45) Date of Patent: \*Feb. 24, 2026

(54) SYSTEM AND METHOD FOR HIGH PRECISION SNAPSHOT MULTI-SPECTRAL IMAGING BASED ON MULTIPLEXED ILLUMINATION

(71) Applicant: Spectral MD, Inc., Dallas, TX (US)

(72) Inventors: Shuai Yu, Mansfield, TX (US); Jason Dwight, Dallas, TX (US); Hanh Le, Rockwall, TX (US); Jeffrey E. Thatcher, Irving, TX (US); Wensheng Fan, Plano, TX (US)

(73) Assignee: Spectral MD, Inc., Dallas, TX (US)

( * ) Notice: Subject to any disclaimer, the term of this patent is extended or adjusted under 35 U.S.C. 154(b) by 53 days.

This patent is subject to a terminal disclaimer.

(21) Appl. No.: 18/470,318

(22) Filed: Sep. 19, 2023

(65) Prior Publication Data

US 2024/0048823 A1     Feb. 8, 2024

Related U.S. Application Data

(63) Continuation of application No. PCT/US2022/022398, filed on Mar. 29, 2022.

(Continued)

(51) Int. Cl.
*H04N 23/11* (2023.01)
*A61B 5/00* (2006.01)
(Continued)

(52) U.S. Cl.
CPC ........... *H04N 23/11* (2023.01); *A61B 5/0075* (2013.01); *A61B 5/7264* (2013.01); *H04N 23/55* (2023.01);
(Continued)

(58) Field of Classification Search
CPC ........ H04N 23/11; H04N 23/55; H04N 23/56; H04N 23/84; A61B 5/0075; A61B 5/7264;
(Continued)

(56) References Cited

U.S. PATENT DOCUMENTS 4,170,987 A     10/1979 Anselmo et al.
4,693,255 A     9/1987 Beall
(Continued)

FOREIGN PATENT DOCUMENTS

CA     2287687     5/2000
CN     1543325     11/2004
(Continued)

OTHER PUBLICATIONS

2011 National Burn Repository: Report of Data from 2001-2010. American Burn Association (2011) pp. 134.
(Continued)

*Primary Examiner* — Nasim N Nirjhar
(74) *Attorney, Agent, or Firm* — Knobbe Martens Olson & Bear LLP

(57) ABSTRACT

The present technology comprises a single-aperture snapshot multi-spectral imaging device generally consisting of at least a color camera, a customized Octa-Band optical filter, a motorized zoom lens, and an 8-wavelength multi-color LED illumination system. The present technology also comprises a method about designing time sequences and combinations of LED illuminations, along with an unmixing algorithm for 8 MSI images generation. According to the present device and method, it is capable of fast multi-spectral image acquisition speed (<100 milliseconds), fast post-processing speed based on adopting a single aperture system without disparity correction calculation, adjustable (Continued)

FOVs, smaller form factors and lower costs, and high precision of spectral information.

30 Claims, 14 Drawing Sheets
(12 of 14 Drawing Sheet(s) Filed in Color)

Related U.S. Application Data

(60) Provisional application No. 63/168,151, filed on Mar. 30, 2021.

(51) Int. Cl.

| | |
|---|---|
| *H04N 23/55* | (2023.01) |
| *H04N 23/56* | (2023.01) |
| *H04N 23/84* | (2023.01) |

(52) U.S. Cl.
CPC ............. *H04N 23/56* (2023.01); *H04N 23/84* (2023.01); *A61B 2576/00* (2013.01)

(58) Field of Classification Search
CPC .......... A61B 2576/00; G01J 2003/1226; G01J 3/0208; G01J 3/0272; G01J 3/513; G01J 3/10; G01J 2003/102; G01J 2003/2806; G01J 2003/2826; G01J 2003/283; G01J 3/28

See application file for complete search history.

(56) References Cited

U.S. PATENT DOCUMENTS

| | | | |
|---|---|---|---|
| 5,074,306 | A | 12/1991 | Green et al. |
| 5,701,902 | A | 12/1997 | Vari et al. |
| 5,982,497 | A | 11/1999 | Hopkins |
| 6,008,889 | A | 12/1999 | Zeng et al. |
| 6,058,352 | A | 5/2000 | Lu et al. |
| 6,081,612 | A | 6/2000 | Gutkowicz-Krusin et al. |
| 6,352,517 | B1 | 3/2002 | Flock et al. |
| 6,353,753 | B1 | 3/2002 | Flock et al. |
| 6,381,488 | B1 | 4/2002 | Dickey et al. |
| 6,411,907 | B1 | 6/2002 | Lu et al. |
| 6,638,668 | B2 | 10/2003 | Buchsbaum et al. |
| 6,640,132 | B1 | 10/2003 | Freeman et al. |
| 6,889,075 | B2 | 5/2005 | Marchitto et al. |
| 7,433,042 | B1 | 10/2008 | Cavanaugh et al. |
| 7,612,822 | B2 | 11/2009 | Ajito et al. |
| 7,648,808 | B2 | 1/2010 | Buchsbaum et al. |
| 7,729,750 | B2 | 6/2010 | Tromberg et al. |
| 7,733,389 | B2 | 6/2010 | Kurosawa et al. |
| 7,835,002 | B2 | 11/2010 | Muhammed et al. |
| 7,860,554 | B2 | 12/2010 | Leonardi et al. |
| 8,081,311 | B2 | 12/2011 | Themelis |
| 8,233,148 | B2 | 7/2012 | Bodkin et al. |
| 8,488,024 | B2 | 7/2013 | Yano et al. |
| 8,509,879 | B2 | 8/2013 | Dukin et al. |
| 8,583,216 | B2 | 11/2013 | Pershing et al. |
| 8,605,172 | B2 | 12/2013 | Nikkanen et al. |
| 8,655,433 | B2 | 2/2014 | Freeman et al. |
| 8,692,912 | B2 | 4/2014 | Fish et al. |
| 8,704,917 | B2 | 4/2014 | Rodrigues et al. |
| 8,812,083 | B2 | 8/2014 | Papazoglou et al. |
| 8,838,211 | B2 | 9/2014 | Melendez et al. |
| 8,892,192 | B2 | 11/2014 | Cuccia et al. |
| 9,031,306 | B2 | 5/2015 | Parvin et al. |
| 9,078,619 | B2 | 7/2015 | Panasyuk et al. |
| 9,295,402 | B1 | 3/2016 | Arbab et al. |
| 9,372,118 | B1 | 6/2016 | Tablin et al. |
| 9,547,178 | B2 | 1/2017 | Erdogan et al. |
| 9,648,254 | B2 | 5/2017 | Darty et al. |
| 9,717,417 | B2 | 8/2017 | DiMaio et al. |
| 9,766,382 | B2 | 9/2017 | Darty |
| 9,962,090 | B2 | 5/2018 | DiMaio et al. |
| 9,990,472 | B2 | 6/2018 | Gurcan et al. |
| 9,996,925 | B2 | 6/2018 | Pedersen et al. |
| 10,066,997 | B2 | 9/2018 | Körner et al. |
| 10,248,713 | B2 | 4/2019 | Pallath et al. |
| 10,740,884 | B2 | 8/2020 | McCall et al. |
| 10,750,992 | B2 | 8/2020 | Fan et al. |
| 10,783,632 | B2 | 9/2020 | Fan et al. |
| 11,182,888 | B2 | 11/2021 | McCall et al. |
| 11,195,281 | B1 | 12/2021 | Schoess et al. |
| 11,304,604 | B2 | 4/2022 | DiMaio et al. |
| 11,337,643 | B2 | 5/2022 | Fan et al. |
| 11,599,998 | B2 | 3/2023 | Fan et al. |
| 11,631,164 | B2 | 4/2023 | McCall et al. |
| 11,948,300 | B2 | 4/2024 | Fan et al. |
| 11,989,860 | B2 | 5/2024 | McCall et al. |
| 2002/0016533 | A1 | 2/2002 | Marchitto et al. |
| 2002/0044691 | A1 | 4/2002 | Matsugu |
| 2004/0239923 | A1 | 12/2004 | Adams et al. |
| 2005/0025118 | A1 | 2/2005 | Hao et al. |
| 2005/0033145 | A1 | 2/2005 | Graham et al. |
| 2005/0254704 | A1 | 11/2005 | Komiya et al. |
| 2006/0155193 | A1 | 7/2006 | Leonardi et al. |
| 2006/0184043 | A1 | 8/2006 | Tromberg et al. |
| 2006/0241495 | A1 | 10/2006 | Kurtz |
| 2007/0016079 | A1 | 1/2007 | Freeman et al. |
| 2007/0024946 | A1 | 2/2007 | Panasyuk et al. |
| 2007/0038042 | A1 | 2/2007 | Freeman et al. |
| 2007/0179482 | A1 | 8/2007 | Anderson |
| 2007/0232930 | A1 | 10/2007 | Feeman et al. |
| 2007/0249913 | A1 | 10/2007 | Freeman et al. |
| 2008/0194928 | A1 | 8/2008 | Bandic et al. |
| 2008/0278602 | A1 | 11/2008 | Otsu |
| 2008/0294032 | A1 | 11/2008 | Levenson et al. |
| 2009/0072142 | A1 | 3/2009 | Blitzer |
| 2009/0118600 | A1 | 5/2009 | Ortiz et al. |
| 2009/0118622 | A1 | 5/2009 | Dukin et al. |
| 2009/0275808 | A1 | 11/2009 | DiMaio et al. |
| 2009/0275841 | A1 | 11/2009 | Melendez et al. |
| 2009/0309960 | A1 | 12/2009 | Park et al. |
| 2010/0042004 | A1 | 2/2010 | Dhawan |
| 2010/0056928 | A1* | 3/2010 | Zuzak ................... G01J 3/2823 356/302 |
| 2010/0111396 | A1 | 5/2010 | Boucheron |
| 2010/0210931 | A1 | 8/2010 | Cuccia |
| 2010/0292549 | A1 | 11/2010 | Shuler |
| 2011/0117025 | A1 | 5/2011 | Dacosta et al. |
| 2011/0124987 | A1 | 5/2011 | Papazoglou et al. |
| 2011/0124988 | A1 | 5/2011 | Cuccia |
| 2011/0205052 | A1 | 8/2011 | Clawson |
| 2012/0078088 | A1 | 3/2012 | Whitestone et al. |
| 2012/0141000 | A1 | 6/2012 | Jeanne et al. |
| 2012/0172243 | A1 | 7/2012 | Davicioni et al. |
| 2012/0190944 | A1 | 7/2012 | Thaveeprungsriporn et al. |
| 2012/0195486 | A1 | 8/2012 | Kirenko et al. |
| 2012/0200700 | A1 | 8/2012 | Bennett et al. |
| 2012/0209095 | A1 | 8/2012 | Huiku |
| 2012/0242870 | A1 | 9/2012 | Koizumi |
| 2012/0245473 | A1 | 9/2012 | Mycek et al. |
| 2012/0288230 | A1 | 11/2012 | Pologe et al. |
| 2012/0307056 | A1 | 12/2012 | Zuzak et al. |
| 2012/0321759 | A1 | 12/2012 | Marinkovich et al. |
| 2013/0021447 | A1 | 1/2013 | Brisedoux et al. |
| 2013/0027543 | A1 | 1/2013 | Boeykens et al. |
| 2013/0051651 | A1 | 2/2013 | Leary et al. |
| 2013/0064441 | A1 | 3/2013 | Kask |
| 2013/0137961 | A1 | 5/2013 | Barnes et al. |
| 2013/0274612 | A1 | 10/2013 | Cuccia et al. |
| 2013/0342670 | A1 | 12/2013 | Kyal et al. |
| 2014/0012225 | A1 | 1/2014 | Yoo et al. |
| 2014/0092288 | A1 | 4/2014 | Hattery et al. |
| 2014/0128744 | A1 | 5/2014 | Cuccia et al. |
| 2014/0155757 | A1 | 6/2014 | Yang et al. |
| 2014/0155818 | A1 | 6/2014 | Salinas et al. |
| 2014/0193050 | A1 | 7/2014 | Miller |
| 2014/0193061 | A1 | 7/2014 | Miller |
| 2014/0213910 | A1 | 7/2014 | Durkin et al. |
| 2014/0257113 | A1 | 9/2014 | Panasyuk et al. |
| 2015/0011892 | A1 | 1/2015 | Sostek |
| 2015/0025342 | A1 | 1/2015 | Papazoglou et al. |
| 2015/0044098 | A1 | 2/2015 | Smart et al. |

(56) References Cited

U.S. PATENT DOCUMENTS

| | | |
|---|---|---|
| 2015/0051498 A1 | 2/2015 | Darty |
| 2015/0080742 A1 | 3/2015 | Andre et al. |
| 2015/0119721 A1 | 4/2015 | Pedersen et al. |
| 2015/0141839 A1 | 5/2015 | Cuccia et al. |
| 2015/0177429 A1 | 6/2015 | Darty |
| 2015/0190061 A1 | 7/2015 | Godavarty et al. |
| 2015/0208923 A1 | 7/2015 | Akl et al. |
| 2015/0223695 A1 | 8/2015 | Chong |
| 2015/0285685 A1 | 10/2015 | Wax et al. |
| 2015/0369664 A1 | 12/2015 | Garsha et al. |
| 2015/0374276 A1 | 12/2015 | Farkas et al. |
| 2015/0374309 A1 | 12/2015 | Farkas et al. |
| 2016/0000395 A1 | 1/2016 | Perumpanani et al. |
| 2016/0033328 A1 | 2/2016 | Walters |
| 2016/0100790 A1 | 4/2016 | Cantu et al. |
| 2016/0245698 A1 | 8/2016 | Pau et al. |
| 2016/0321414 A1 | 11/2016 | Salganicoff et al. |
| 2016/0345888 A1 | 12/2016 | Wu et al. |
| 2016/0349228 A1 | 12/2016 | Kester et al. |
| 2017/0079530 A1* | 3/2017 | DiMaio ............... A61B 5/0261 |
| 2017/0084024 A1 | 3/2017 | Gurevich |
| 2017/0135646 A1 | 5/2017 | Chin |
| 2017/0150903 A1 | 6/2017 | Barnes et al. |
| 2017/0167980 A1 | 6/2017 | Dimitriadis et al. |
| 2017/0178322 A1 | 6/2017 | Hakuk et al. |
| 2017/0223316 A1 | 8/2017 | Zeng et al. |
| 2017/0262984 A1 | 9/2017 | Barnes et al. |
| 2017/0272666 A1 | 9/2017 | Darty et al. |
| 2017/0299435 A1 | 10/2017 | Rhoads et al. |
| 2017/0319073 A1 | 11/2017 | DiMaio et al. |
| 2017/0354358 A1 | 12/2017 | Rajab |
| 2017/0367580 A1 | 12/2017 | DiMaio et al. |
| 2018/0028079 A1 | 2/2018 | Gurevich et al. |
| 2018/0061046 A1 | 3/2018 | Bozorgtabar et al. |
| 2018/0176488 A1 | 6/2018 | Dvir |
| 2018/0184015 A1 | 6/2018 | Richarte et al. |
| 2018/0226154 A1 | 8/2018 | Gurcan et al. |
| 2018/0237783 A1 | 8/2018 | Dallas et al. |
| 2018/0245978 A1 | 8/2018 | Wang et al. |
| 2018/0247153 A1 | 8/2018 | Ganapati et al. |
| 2018/0310828 A1 | 11/2018 | DiMaio et al. |
| 2019/0057268 A1 | 2/2019 | Burge et al. |
| 2019/0082998 A1 | 3/2019 | Nowroozi et al. |
| 2019/0277753 A1 | 9/2019 | Waxman et al. |
| 2019/0290117 A1 | 9/2019 | Wang et al. |
| 2020/0137301 A1* | 4/2020 | Fields ................... H04N 23/689 |
| 2020/0138360 A1 | 5/2020 | Fan et al. |
| 2020/0193580 A1 | 6/2020 | McCall et al. |
| 2020/0193597 A1 | 6/2020 | Fan et al. |
| 2021/0082094 A1 | 3/2021 | McCall et al. |
| 2021/0169400 A1 | 6/2021 | Fan et al. |
| 2021/0201479 A1 | 7/2021 | Fan et al. |
| 2022/0142484 A1 | 5/2022 | DiMaio et al. |
| 2022/0156903 A1 | 5/2022 | McCall et al. |
| 2022/0240783 A1 | 8/2022 | Fan et al. |
| 2023/0148951 A1 | 5/2023 | Thatcher et al. |
| 2023/0181042 A1 | 6/2023 | Fan et al. |
| 2023/0206413 A1 | 6/2023 | McCall et al. |
| 2023/0222654 A1 | 7/2023 | Fan et al. |
| 2024/0281966 A1 | 8/2024 | Fan et al. |
| 2025/0005761 A1 | 1/2025 | Thatcher et al. |

FOREIGN PATENT DOCUMENTS

| | | |
|---|---|---|
| CN | 1745294 | 3/2006 |
| CN | 1784185 | 6/2006 |
| CN | 101394782 | 3/2009 |
| CN | 101627902 | 1/2010 |
| CN | 101784227 | 7/2010 |
| CN | 102099671 | 6/2011 |
| CN | 102598683 | 7/2012 |
| CN | 102641126 | 8/2012 |
| CN | 103228205 | 7/2013 |
| CN | 103973957 | 8/2014 |
| CN | 103815875 | 6/2015 |
| CN | 105143448 | 12/2015 |
| CN | 103327894 | 5/2016 |
| CN | 105636512 | 6/2016 |
| CN | 106580328 A | 4/2017 |
| CN | 106714670 | 5/2017 |
| CN | 107209934 | 9/2017 |
| CN | 107483774 | 12/2017 |
| CN | 107750345 | 3/2018 |
| CN | 108053482 | 5/2018 |
| CN | 108882896 | 11/2018 |
| EP | 1531629 | 5/2005 |
| EP | 2944930 | 11/2015 |
| EP | 2955496 | 12/2015 |
| JP | H05-505117 | 8/1993 |
| JP | H08-320287 | 12/1996 |
| JP | H10-505768 | 6/1998 |
| JP | 2000-139846 | 5/2000 |
| JP | 2001-503645 | 3/2001 |
| JP | 2005-502895 | 1/2005 |
| JP | 2008-525158 | 7/2008 |
| JP | 2008-283692 | 11/2008 |
| JP | 2010-021614 | 1/2010 |
| JP | 2010-043979 | 2/2010 |
| JP | 2010-503475 | 2/2010 |
| JP | 2011-521237 | 7/2011 |
| JP | 2015-523135 | 8/2015 |
| JP | 2016-540622 | 12/2016 |
| JP | 2017-524935 | 8/2017 |
| JP | 2017-529514 | 10/2017 |
| JP | 2018-036177 | 3/2018 |
| JP | 2018-534965 | 11/2018 |
| JP | 2019-211475 | 12/2019 |
| JP | 2020-046489 | 3/2020 |
| JP | 2022-513486 | 2/2022 |
| RU | 2459574 C1 | 8/2012 |
| TW | 512058 | 12/2002 |
| WO | WO 98/33813 | 8/1998 |
| WO | WO 03/025546 | 3/2003 |
| WO | WO 2004/005895 | 1/2004 |
| WO | WO 2004/012461 | 2/2004 |
| WO | WO 2008/105370 | 9/2008 |
| WO | WO 2009/131989 | 10/2009 |
| WO | WO 2009/140757 | 11/2009 |
| WO | WO 2014/007869 | 1/2014 |
| WO | WO 2014/041543 | 3/2014 |
| WO | WO 2014/125250 | 8/2014 |
| WO | WO 2014/143235 | 9/2014 |
| WO | WO 2015/116823 | 8/2015 |
| WO | WO 2015/185662 | 12/2015 |
| WO | WO 2016/069788 | 5/2016 |
| WO | WO 2016/088483 | 6/2016 |
| WO | WO 2016/153741 A1 | 9/2016 |
| WO | WO 2017/026296 | 2/2017 |
| WO | WO 2017/053609 | 3/2017 |
| WO | WO 2017/074505 | 5/2017 |
| WO | WO 2017/086788 | 5/2017 |
| WO | WO 2017/202535 | 11/2017 |
| WO | WO 2017/223206 | 12/2017 |
| WO | WO 2018/018160 | 2/2018 |
| WO | WO 2018/160963 | 9/2018 |
| WO | WO 2018/217162 | 11/2018 |
| WO | WO 2020/123722 | 6/2020 |
| WO | WO 2020/123724 A1 | 6/2020 |
| WO | WO 2020/123724 A4 | 6/2020 |
| WO | WO 2021/173763 | 9/2021 |
| WO | WO-2021202438 A1 * | 10/2021 | ........... A61B 5/0095 |
| WO | WO 2022/015597 | 1/2022 |
| WO | WO 2022/212413 | 10/2022 |
| WO | WO 2023/141216 | 7/2023 |
| WO | WO 2023/141216 A2 | 7/2023 |

OTHER PUBLICATIONS

Afromowitz et al., "Clinical Evaluation of Burn Injuries Using an Optical Reflectance Technique," IEEE Transactions on Biomedical Engineering, 1987; 34(2):114-27.

(56)                    References Cited

OTHER PUBLICATIONS

Afromowitz et al., "Multispectral imaging of burn wounds: a new clinical instrument for evaluating burn depth". IEEE transactions on bio-medical engineering, 1988; 35(10):842-850.

Aldrich, John, "R. A. Fisher and the Making of Maximum likelihood 1912-1922", Statistical Science, 1997; 12(3):162-176.

Alian et al., "Photoplethysmography," Best Pract. Res. Clin. Anaesthesiol., 2014; 28(4):395-406; ePub Sep. 9, 2014.

Allen, John, "Photoplethysmography and its application in clinical physiological measurement.," Physiol. Meas., 2007; 28:R1-R39.

Anselmo et al., "Multispectral Photographic Analysis—A New Quantitative Tool to Assist in the Early Diagnosis of Thermal Burn Depth." Annals Of Biomed Engin. 1977; 5:179-193.

Antonutto et al., "Noninvasive assessment of cardiac output from arterial pressure profiles during exercise," Eur J Appl Physiol. 1995; 72:18-24.

Arsenault et al., "The Use of Transcutaneous Oximetry to Predict Healing Complications of Lower Limb Amputations: A Systematic Review and Meta-Analysis," Eur J Vasc Endovasc Surg. 2012; 43:329-336.

Badrinarayanan et al., "SegNet: A Deep Convolutional Encoder-Decoder Architecture for Image Segmentation", IEEE Transactions on Pattern Analysis and Machine Intelligence, Oct. 2016, vol. 39, No. 12, pp. 2481-2495.

Badrinarayanan et al., "SegNet: A Deep Convolutional Encoder-Decoder Architecture for Robust Semantic Pixel-Wise Labelling", Computer Science, CVPR 2015, https://arxiv.org/abs/1505.07293, May 2015.

Bajwa et al., "Assessment of Tissue Perfusion in the Lower Limb: Current Methods and Techniques Under Development," Circ Cardiovasc Imag. Sep. 2014; 7:836-843.

Bak et al., "Hemodynamic Changes During Resuscitation After Burns Using The Parkland Formula". J Trauma-Injury Infect Crit Care, 2009; 66(2):329-336.

Baxter, R.D. et al., "Development of a Non-Invasive Imaging Device for Prediction of Diabetic Foot Ulcer Healing Potential", Poster presented at Symposium on Advanced Wound Care, May 7-11, 2019, in 2 pages.

Benitez et al., "Contemporary assessment of foot perfusion in patients with critical limb ischemia," Semin Vasc Surg. Mar. 2014; 27:3-15.

Blanpain et al., "Epidermal homeostasis: A balancing act of stem cells in the skin", Nature Reviews Molecular Cell Biology, Mar. 2009, vol. 10, pp. 207-217.

Branski et al., "A porcine model of full-thickness burn, excision, and skin autografting," Burns 2008; 34(8):1119-1127.

Burgess et al., "Segmental Transcutaneous Measurements of PO2 in Patients Requiring Below-The-Knee Amputation for Peripheral Vascular Insufficiency," J Bone Jt Surg Am 1982; 64:378-82.

Cancio et al., "Burn Support for Operation Iraqi Freedom and related operations, 2003 to 2004", J Burn Care Rehabil. (2005) 26(2): 151-161.

CDC, Diabetes Public Health Resource, "Number (in Thousands) of Hospital Discharges for Non-Traumatic Lower Extremity Amputation with Diabetes as a Listed Diagnosis, United States, 1988-2006," Centers for Disease Control and Prevention, Oct. 20, 2016, Available at: http://www.cdc.gov/diabetes/statistics/lea/fig1.htm; 3 pages.

Cheong et al., "A Review of the Optical Properties of Biological Tissues", IEEE J Quantum Electronics; 1990; 26(12): 2166-2185.

Cortes et al., "Support-Vectors Networks," Machine Learning 1995; 20:273-297.

Cousineau et al., "Outliers detection and treatment: a review," Inter J Psycholog Res. 2010; 3(1):58-67.

Cover et al., "Nearest Neighbor Pattern Classification", IEEE Transactions on Information Theory; 1967; 13(1):21-27.

Cross et al., "Clinical Utilization of Near-infrared Spectroscopy Devices for burn depth assessment", Wound Rep Reg. (2007) 15: 332-340.

Cross et al., "Near infrared point and imaging spectroscopy for burn depth assessment", Int'l Congress Series (2005) 1281: 137-142.

Cuccia et al., "Quantitation and mapping of tissue optical properties using modulated imaging," J Biomed Opt., 2009; 14(2): 1-31.

Desai et al., "Early Burn Wound Excision Significantly Reduces Blood Loss," Ann. Surg. 1990; 211(6):753-762.

Devagn et al., "Modalities for the Assessment of Burn Wound Depth", Journal of Burns and Wounds, Feb. 2006, vol. 5, pp. 7-15.

Dillingham et al., "Reamputation, Mortality, and Health Care Costs Among Persons with Dysvascular Lower-Limb Amputations," Arch Phys Med Rehabil. 2005; 86:480-486.

Downing et al., "Multi-aperture hyperspectral imaging", Applied Industrial Optics: Spectroscopy, Imaging, and Metrology, Jun. 2013, in 3 pages.

Duda et al., *Pattern Classification*, Second Edition, John Wiley & Sons, Nov. 2000.

Eisenbeiss et al., "Reflection-optical multispectral imaging method for objective determination of burn depth," Burns. 1999; 25:697-704.

Elmasry et al., "Chapter 1: Principles of Hyperspectral Imaging Technology", *Hyperspectral Imaging for Food Quality Analysis and Control*, Dec. 2010, pp. 3-43.

Eneroth, M., "Factors affecting wound healing after major amputation for vascular disease: a review," Prosth Ortho Internat. 1999; 23:195-208.

Engrav et al., "Early Excision and Grafting vs. Nonoperative Treatment of Burns of Indeterminant Depth: A Randomized Prospective Study," J of Trauma, 1983; 23(11):1001-1004.

Fischer et al., "Multispectral and Hyperspectral imaging technologies in conservation: current research and potential applications," Stud Conserv. 2006; 7: 3-16.

Franklin et al., "Cost of lower-limb amputation in US veterans with diabetes using health services data in fiscal years 2004 and 2010," J Rehabil Res Dev (JRRD) 2014; 51(8):1325-1330.

Garcin et al., "Hair Follicle Bulge Stem Cells Appear Dispensable for the Acute Phase of Wound Re-epithelialization", Stem Cells, Jan. 2016, vol. 34, pp. 1377-1385.

Graham et al., "Wound Healing of Cutaneous Sulfur Mustard Injuries: Strategies for the Development of Improved Therapies," J Burns and Wounds. 2005; 4:1-45.

Grubbs, Frank E., "Procedures for detecting outlying observations in samples", Ballistic Research Laboratories, Aberdeen Proving Ground, 1974; BRL Report No. 1713; 53 pages.

Grubbs, Frank E., "Procedures for Detecting Outlying Observations in Samples", Technometrics, vol. 11(1), Feb. 1969, pp. 1-21.

Guo et al., "Factors Affecting Wound Healing," J Dent Res. 2010; 89(3):219-229.

Gurfinkel et al., "Development of a Novel Animal Burn Model Using Radiant Heat in Rats and Swine," Acad Emerg Med. 2010; 17(5):514-520.

Gurfinkel et al., "Histological assessment of tangentially excised burn eschars," Can J Plast Surg. 2010; 18(3):e33-e36.

Gurtner et al., "Wound repair and regeneration", Nature, May 2008, vol. 453, pp. 314-321.

Guyon et al., "An Introduction to Variables and Feature Selection", J Machine Learn Res. 2003; 3:1157-1182.

Haberal et al., "Fluid management in major burn injuries", Indian J. Plast. Surg., Sep. 2010, vol. 43(Suppl), S29-S36.

HCUP Nationwide Inpatient Sample (NIS)—2009, Healthcare Cost and Utilization Project—HCUP, A Federal-State-Industry Partnership in Health Data Issued May 2011, Updated Nov. 2015, 89 pages, Retrievable at http://www.hcup-us.ahrq.gov; 89 pages.

Heimbach et al., "Burn depth: A review", World Journal of Surgery, Jan.-Feb. 1992, vol. 16, pp. 10-15.

Heimbach et al., *Surgical management of the burn wound*, Cover and Table of Contents, New York: Raven Press, 1984; TOC only.

Heimbach, David M., "Early Burn Excision and Grafting," Surgical Clinics of North America [Burns], 1987; 67(1):93-107.

Heredia-Juesas et al., "Non-Invasive Optical Imaging Techniques for Burn-Injured Tissue Detection for Debridement Surgery," Conf Proc IEEE/EMBS, Aug. 2016; 2893-2896.

(56) References Cited

OTHER PUBLICATIONS

Hu et al., "Development of Effective Photoplethysmographic Measurement Techniques: From Contact to Non-Contact and from Point to Imaging." 31st Annual International Conference of the IEEE/EMBS. 2009; 6550-6553.

Huot et al., "Time-resolved multispectral imaging of combustion reaction", Proc. SPIE 9485, Thermosense: Thermal Infrared Applications XXXVII, 94851C, May 2015.

HyperMed Imaging Inc., FDA-DHHS Reply to 510(k), "Hyperview Hyperspectral Tissue Oxygenation Measurement System" dated Dec. 16, 2016 with enclosures; in 15 pages.

HyperMed Medical Spectral Imaging, Product Overview "HyperView", 2017 in 4 pages.

IMEC, "Hyperspectral Imaging", downloaded from https://www.imec-int.com/en/hyperspectral-imaging on Jul. 24, 2018 in 10 pages.

Imms et al., "A high performance biometric signal and image processing method to reveal blood perfusion towards 3D oxygen saturation mapping", Progress Biomed Optics & Imaging [SPIE] (2014) 8947:89470 in 11 pages.

Ioffe et al., "Batch Normalization: Acceleration Deep Network Training by Reducing Internal Covariate Shift", 2015, arXiv:1502.03167v3, https://arxiv.org/abs/1502.03167.

Israel et al., "Variations in Burn Excision and Grafting: A Survey of the American Burn Association", J Burn Care Res. (2017) 38(1): 125-132.

Ito et al., "Stem cells in the hair follicle bulge contribute to wound repair but not to homeostasis of the epidermis", Nature Medicine, Dec. 2005, vol. 11, pp. 1351-1354.

Jackson D. "The diagnosis of the depth of burning." Br J Surg. 1953; 40:588-596.

Jacques et al., "Absorption spectra for biological tissues," ECE532 Biomedical Optics, 1998, Available from: http://omlc.org/education/ece532/class3/muaspectra.html; 1 page.

Jacques, Steven L., "Optical properties of biological tissues: A review", Phys Med. Biol., 2013, 58 (12), R37-61 and Corrigendum 2013 58:5007-5008.

Jaskille et al., "Critical Review of burn depth assessment techniques: Part II. Review of Laser Doppler Technology", J Burn Care Res. (2010) 31(1): 151-157.

Jolivot et al., "Skin Parameter Map Retrieval from a Dedicated Multispectral Imaging System Applied to Dermatology/Cosmetology", International Journal of Biomedical Imaging, Sep. 2013; vol. 3:978289, in 16 pages.

Jones et al., "Snapshot Spectral Imaging Technologies for On-Site Inspection", Presentation given at CTBTO Science and Technology 2015 (SnT2015) Jun. 26, 2015; Vienna, Austria; in 20 pages.

Kaiser et al., "Noninvasive assessment of burn wound severity using optical technology: A review of current and future modalities." Burns. 2011; 37(3): 377-386.

Kauvar et al., "Comparison of Combat and Non-Combat Burns from Ongoing U.S. Military Operations", J Surg Res. (2006) 132(1): 195-200.

Kearns et al., "Disaster planning: The past, present, and future concepts and principles of managing a surge of burn injured patients for those involved in hospital facility planning and preparedness," J Burn Care Res. Jan./Feb. 2014; 35(1):e33-e42.

Kendall et al., "Bayesian SegNet: Model Uncertainty in Deep Convolutional Encoder-Decoder Architectures for Scene Understanding", Oct. 2016, https://arxiv.org/abs/1511.02680.

King et al., "Surgical wound debridement sequentially characterized in a porcine burn model with multispectral imaging," Burns, 2015; 41:1478-1487.

King, Paul, Book Reviews; "*Design of Pulse Oximeters*," IEEE Eng. Med. Biol. Mag., 1998; p. 117.

Kono et al., "Identifying the incidence of and risk factors for reamputation among patients who underwent foot amputation," Ann Vasc Surg 2012; 26:1120-1126.

Lee et al., "Operative wound management," Chapter 13, © 2012 Elsevier Ltd, Inc, BV, DOI: 10.1016/B978-1-4377-2786-9I00013-8, pp. 157-172e2.

Li et al., "Burn injury diagnostic imaging device's accuracy improved by outlier detection and removal," Proc. Of SPIE, vol. 9472, 2015 SPIE, pp. 947206-1 to 947206-11.

Li et al., "Outlier detection and removal improves accuracy of machine learning approach to multispectral burn diagnostic imaging," J. Bio. Optics. Dec. 2015; 20(12):121305-1 to 121305-9.

Li et al., "Simultaneous measurement of deep tissue blood flow and oxygenation using noncontact diffuse correlation spectroscopy flow-oximeter", Scientific Reports, Feb. 2013, 3:1358, pp. 1-10.

Li et al., "Review of spectral imaging technology in biomedical engineering: achievements and challenges," J Biomed Optics. 2013; 18(10):100901; 29 pages.

Lieberman, J.I. et al., National Preparedness: Countermeasures for Thermal Burns. United States Government Accountability Office. GAO-12-304R, Feb. 22, 2012.

Liu et al., "Toward integrating feature selection algorithms for classification and clustering." IEEE Transactions on Knowledge and Data Engineering. 2005. 17(4): 491-502; 35 pages.

Lu et al., "Medical hyperspectral imaging: A review," J Biomed Optics Jan. 2014; 19(1):0101901, 24 pages.

Macri et al., "Immediate burn excision fails to reduce injury progression," J Burn Care Res. 2013; 34(3):153-160.

Marimont et al., "Nearest Neighbor searches and the curse of Dimensionality," J Inst Math Applics 1979; 24 (1): 59-70.

Mertens et al., "Outpatient Burn Management," Nursing Clinics of North America, Burn Mgmt. 1997; 32(2):343-364.

Meyerholz et al., "Morphological Parameters for Assessment of Burn Severity in an Acute Burn Injury Rat Model", International Journal of Experimental Pathology, 2009, vol. 90, pp. 26-33.

Middelkoop et al., "Porcine wound models for skin substitution and burn treatment," Biomaterials. 2004; 25:1559-1567.

Mo et al., "The importance of illumination in a non-contact photoplethysmography imaging system for burn wound assessment", Proc. SPIE 9303 Photonic Therapeutics and Diagnostics XI, 93030M, Feb. 2015; 10 pages.

Mohler, Emile R., "Screening for Peripheral Artery Disease", Circulation, Aug. 2012, vol. 126:e111-e112, in 2 pages.

Monstrey et al., "Assessment of Burn Depth and Burn Wound Healing Potential", Burns, 2008, vol. 34, pp. 761-769.

Mook et al., "Instruments and techniques: Spectrophotometric determination of oxygen saturation of blood independent of the presence of indocyanine green," Cardiovascular Research, 1979; 13:233-237.

MOOR Instruments, "Early and Accurate Burn Assessment with Laser Doppler Imaging", Product Brochure; Dec. 2014; 16 pages.

Moza et al., "Deep-Tissue Dynamic Monitoring of Decubitus Ulcers: Wound Care and Assessment," IEEE Eng Med Biol Mag. 2010; 29(2):71-77.

National Limb Loss Information Center, "Fact Sheet: Amputation Statistics by Cause: Limb Loss in the United States," National Limb Loss Information Center, Fact Sheet. Revised 2008, 3 pages.

Nehler et al., "Functional outcome in a contemporary series of major lower extremity amputations," J Vasc Surg. 2003; 38:7-14.

Nguyen et al., "Spatial frequency domain imaging of burn wounds in a preclinical model of graded burn severity." J Biomed Optics. 2013; 18(6): 066010; 8 pages.

Nilsson, Lena M. "Respiration Signals from Photoplethysmography.," Anesth Analg. 2013; 117(4):859-65.

Norgren et al., Inter-Society Consensus for the Management of Peripheral Arterial Disease (TASC II), J Vasc Surg. 2007; 45(Supp 1):S5A-S67A.

Nouri et al., "Colour and multispectral imaging for wound healing evaluation in the contextof a comparative preclinical study", Proc Opt Diagnostics of Living Cells II, (2013) 8669:866923 in 11 pages.

Obermeyer et al., "Predicting the Future—Big Data, Machine Learning, and Clinical Medicine", N Engl J Med. (Sep. 2016) 375(13): 1216-1219.

OPTICS.org—The business of photonics, IMEC Launches TDI, multispectral and hyperspectral sensors; News-Release of Feb. 8, 2017; SPIE Europe in 4 pages.

Orgill, D., "Excision and skin grafting of thermal burns," New Eng J Med. 2011; 360:893-901.

(56)                    References Cited

OTHER PUBLICATIONS

Ortiz-Pujols et al., "Burn care: Are there sufficient providers and facilities?" Chapel Hill, North Carolina. American College of Surgeons Health Policy Research Institute, Nov. 2011; 9:4 pages.

Pape et al., "An audit of the use of laser Doppler imaging (LDI) in the assessment of burns of intermediate depth," Burns 2001; 27:233-239.

Papp et al., "The progression of burn depth in experimental burns: A histological and methodological study", Burns, 2004, vol. 30, pp. 684-690.

Peng et al., "Feature Selection Based on Mutual Information: Criteria of Max-Dependency, Max-Relevance, and Min-Redundancy," IEEE Trans. on Pattern Analysis and Machine Intelligence, 2005; 27(8):1226-1238.

Perkins et al., "GENIE: A Hybrid Genetic Algorithm for Feature Classification in Multi- Spectral Images", in *Applications and science of neural networks, fuzzy systems, and evolutionary computation III*; Inter'l Society of Optics and Photonics (2000) 4120:52-63.

Petricoin et al., "SELDI-TOF-based serum proteomic pattern diagnostics for early detection of cancer", Curr Opin Biotechnol. (2004) 15(1): 24-30.

Regensteiner et al, "The impact of peripheral arterial disease on health-related quality of life in the Peripheral Arterial Disease Awareness, Risk, and Treatment: New Resources for Survival (PARTNERS) Program", Vascular Medicine, Feb. 2008, vol. 13:15-24.

Reisner et al., "Utility of the Photoplethysmogram in Circulatory Monitoring", Anesthesiol. 2008; 108:950-958.

Resch et al., "Estimation of burn depth at burn centers in the United States: a survey." J Burn Care Res. Nov./Dec. 2014; 35: 491-497.

RESURGE International, "Burns: The Neglected but Solvable Health Crisis" from Reconstructive Surgery for the World's Poor since 1969; accessed <http://www.resurge.org/transforming_lives/story_burns.cfm> Accessed Feb. 9, 2015; 3 pages.

Rittie, L., "Cellular mechanisms of skin repair in humans and other mammals", Journal of Cell Communication and Signaling, 2016, vol. 10, pp. 103-120.

Robnik-Sikonja et al., "Evaluation of prognostic factors and prediction of chronic wound healing rate by machine learning tools", Artificial Intelligence in Medicine, Jan. 2003, in 10 pages. URL: http://lkm.fri.uni-lj.si/rmarko/papers/robnik01-aime.pdf.

Rogers et al., "The right to bear legs—An amendment to healthcare: how preventing amputations can save billions for the US health-care system," J Am Podiatr Med Assoc 2008; 98:166-168.

Rousseeuw, Peter J. "Least Median of Squares Regression". J Am Stat Assoc. 1984; 79(388):871-880.

Rowan et al., "Burn wound healing and treatment: review and advancements", Critical Care, 2015, vol. 19, in 12 pages.

Severinghaus et al., "History of Blood Gas Analysis. VII. Pulse Oximetry." J Clin Monitor. 1987; 3(2):135-138.

Sheng et al., "BurnCalc assessment study of computer-aided individual three-dimensional burn area calculation", Journal of Translational Medicine, Sep. 2014, vol. 12, p. 242, in 12 pages.

Siew, Ronian [Ed.], Multiple-Field Multispectral Imaging Using Wide-Angle Lenses, Inopticalsolutions Notebook Series (2018); Chapter 1, pp. 1-12.

Singer et al., "A porcine burn model," Meth Mol Med. 2003; 78:107-119.

Singer et al., "Standardized Burn Model Using a Multiparametric Histologic Analysis of Burn Depth", Academic Emergency Medicine, Jan. 2000, vol. 7, pp. 1-6.

Sokolova et al., "A systematic analysis of performance measures for classification tasks." Info Proc Manag. 2009; 45: 427-437.

Sowa et al., "Classification of burn injuries using near-infrared spectroscopy", J Biomed Optics. (Sep. 2006) 11(5): 6 pages.

Sowa et al., "Near infrared spectroscopic assessment of hemodynamic changes in the early post-burn period", Burns (2001) 27: 241-249.

Spectral MD, Inc., "DeepView Digital Video Physiological Portable Imaging System", FDA Traditional 510(k) Application as filed Dec. 28, 2012; 528 pages.

Spigulis et al., "A Device for Multimodal Imaging of Skin", Multimodal Biomedical Imaging VIII, Proc. SPIE, vol. 8574, p. 85740J, Feb. 2013, in 7 pages.

Squiers et al., "Multispectral imaging burn wound tissue classification system: a comparison of test accuracies between several common machine learning algorithms," Proc. Of SPIE, 2016; 9785:97853L-1 to 97853L-10.

Steinberg et al., "Sample size for positive and negative predictive value in diagnostic research using case-control designs", Biostatistics, vol. 10, No. 1, pp. 94-105, 2009.

Takeo et al., "Wound Healing and Skin Regeneration", Cold Spring Harbor Perspectives Medicine, 2015, vol. 5, in 13 pages.

Thatcher et al., "Multispectral and Photophlethysmography Optical Imaging Techniques Identify Important Tissue Characteristics in an Animal Model of Tangential Burn Excision," J Burn Care & Res., Jan./Feb. 2016, 37(1):38-52.

Thatcher et al., "Dynamic tissue phantoms and their use in assessment of a noninvasive optical plethysmography imaging device," SPIE Sensing Technology + Applications, May 2014; 910718, 18 pages.

Thatcher et al., "Imaging Techniques for Clinical Burn Assessment with a Focus on Multispectral Imaging," Advan Wound Care, Mar. 2016; 5(8):360-378.

Themelis et al., "Multispectral Imaging Using Multiple-bandpass filters", Opt Lett., May 2008; 33(9):1023-1025.

Tiwari, V.K., "Burn wound: How it differs from other wounds?" Indian Journal of Plastic Surgery, May-Aug. 2012, vol. 45, pp. 364-373.

Tuchin, Valery V., "Light-Tissue Interactions", Biomedical Photonics Handbook, CRC Press, Boca Raton, Florida 2003; Chapter 3; pp. 123-167.

Usman et al., "Second Derivative of Photoplethysmogram in Estimating Vascular Aging Among Diabetic Patients," in Internet Conf for Technical Postgraduates 2009, TECHPOS 2009, 3 pages.

Vemulapalli et al., "Peripheral arterial testing before lower extremity amputation among Medicare beneficiaries, 2000 to 2010," Circ Cardiovasc Qual Outcomes, Jan. 2014, 7:142-150.

Vogel et al., "Using Non-Invasive Multi-Spectral Imaging to Quantitatively Assess Tissue Vasculature", J Biomed Optics (2007) 12(5): 051604 in 32 pages.

Wang et al., "A Unified Framework for Automatic Wound Segmentation and Analysis with Deep Convolutional Neural Networks", 2015 37th Annual International Conference of the IEEE Engineering in Medicine and Biology Society (EMBC), Aug. 2015, pp. 2415-2418.

Waters et al., "Energy cost of walking of amputees: the influence of level of amputation," J Bone Joint Surg. 1975; 58(1):42-46.

Watts et al., "Burn depth and its histological measurement," Burns 27 (2001) 154-160.

Webb, Steve [Ed.], *The physics of medical imaging*, © 1988, IOP Publishing Ltd., TOC only.

Webster, J.G. [Ed.], *Design of Pulse Oximeters*, Medical Science Series, © IOP Publishing Ltd. 1997; TOC only.

Worsley et al., "Back to basics: biophysical methods in tissue viability research," (Draft); J Wound Care, 2013; 22(8):434-439.

Wütschert et al., "Determination of Amputation Level in Ischemic Limbs—Reappraisal of the measurement of TcPo$_2$", Diabetes Care, 1997; 20(8):1315-1318.

Xie et al., "Skin appendage-derived stem cells: cell biology and potential for wound repair", Burns and Trauma, 2016, vol. 4(38), in 6 pages.

Ziegler-Graham et al., "Estimating the Prevalence of Limb Loss in the United States: 2005 to 2050," Arch Phys Med Rehabil. 2008; 89:422-429.

Zonios et al., "Skin melanin, hemoglobin, and light scattering properties can be quantitatively assessed in vivo using diffuse reflectance spectroscopy", J Invest Dermatol. (2001) 117(6): 1452-1457.

International Search Report and Written Opinion dated Jul. 26, 2022 for PCT/US2022/022398.

(56)                    References Cited

OTHER PUBLICATIONS

"MC85 Gangrene", ICD-11 for Mortality and Morbidity Statistics, World Health Organization, webpage accessed Apr. 3, 2024, in 1 page. URL: https://icd.who.int/browse/2024-01/mms/en#188156827.

Cai, S. et al., "Multi-view distributed video coding using epipolar geometry", Computer Engineering and Applications, 2010, vol. 46(17), pp. 121-124.

El Gamal, A. et al., "CMOS Image Sensors: An introduction to the technology, design and performance limits, presenting recent developments and future directions", IEEE Circuits and Devices Magazine, 2005, vol. 21(3), pp. 6-20.

Mukherjee, R. et al., "Diagnostic and Prognostic Utility of Non-Invasive Multimodal Imaging in Chronic Wound Monitoring: a Systemic Review", Journal of Medical Systems, Feb. 2017, vol. 41, No. 3, in 17 pages.

Pan, Z-W et al., "Fast Multispectral Imaging by Spatial Pixel-Binning and Spectral Unmixing", IEEE Transactions on Image Processing, Aug. 2016, vol. 25, No. 8, pp. 3612-3625. doi: 10.1109/TIP.2016.2576401.

Yang, Q. et al., "Investigation of the Performance of Hyperspectral Imaging by Principal Component Analysis in the Prediction of Healing of Diabetic Foot Ulcers", Journal of Imaging, Dec. 2018, vol. 4, No. 12, in 11 pages.

Goyal, M. et al., "Fully convolutional networks for diabetic foot ulcer segmentation", 2017 IEEE International Conference on Systems, Man, and Cybernetics (SMC), 2017, pp. 618-623. doi: 10.1109/SMC.2017.8122675.

Scholz, I., "Reconstruction and Modeling of Static and Dynamic Light Fields", University of Erlangen-Nürnberg, Jan. 2008, pp. 1-268. URL: https://citeseerx.ist.psu.edu/viewdoc/download?doi=10.1.1.643.3427&rep=rep1&type=pdf.

* cited by examiner

120

Short Blue
Green
Yellow
Red Orange
Deep Red
Far Red
Non-PPG NIR
PPG NIR

SYSTEM AND METHOD FOR HIGH PRECISION SNAPSHOT MULTI-SPECTRAL IMAGING BASED ON MULTIPLEXED ILLUMINATION

CROSS-REFERENCE TO RELATED APPLICATIONS

This application is a continuation of International Application No. PCT/US2022/022398, filed Mar. 29, 2022, entitled "SYSTEM AND METHOD FOR HIGH PRECISION SNAPSHOT MULTI-SPECTRAL IMAGING BASED ON MULTIPLEXED ILLUMINATION," which claims the benefit of U.S. Provisional Application Ser. No. 63/168,151, filed Mar. 30, 2021, entitled "SYSTEM AND METHOD FOR HIGH PRECISION SNAPSHOT MULTI-SPECTRAL IMAGING BASED ON MULTIPLEXED ILLUMINATION," both of which are hereby expressly incorporated by reference in their entirety and for all purposes.

STATEMENT REGARDING FEDERALLY SPONSORED R&D

Some of the work described in this disclosure was made with United States Government support under Contract No. HHS0100201300022C, awarded by the Biomedical Advanced Research and Development Authority (BARDA), within the Office of the Assistant Secretary for Preparedness and Response in the U.S. Department of Health and Human Services. Some of the work described in this disclosure was made with United Government support under Contract Nos. W81XWH-17-C-0170 and/or W81XWH-18-C-0114, awarded by the U.S. Defense Health Agency (DHA). The United States Government may have certain rights in this invention.

TECHNICAL FIELD

The systems and methods disclosed herein are directed to spectral imaging, and, more particularly, to systems and methods for multi-spectral imaging using multiplexed illumination.

BACKGROUND

The electromagnetic spectrum is the range of wavelengths or frequencies over which electromagnetic radiation (e.g., light) extends. In order from longer wavelengths to shorter wavelengths, the electromagnetic spectrum includes radio waves, microwaves, infrared (IR) light, visible light (that is, light that is detectable by the structures of the human eye), ultraviolet (UV) light, x-rays, and gamma rays. Spectral imaging refers to a branch of spectroscopy and photography in which some spectral information or a complete spectrum is collected at locations in an image plane. Multispectral imaging systems can capture multiple spectral bands (on the order of a dozen or less and typically at discrete spectral regions), for which spectral band measurements are collected at each pixel, and can refer to bandwidths of about tens of nanometers per spectral channel.

The spectral bands may be separated by optical filters and/or multi-channel image sensors (e.g., color cameras). A FilterWheel based single-aperture multi-spectral imaging system provides high spectral precision yet is limited by slow temporal resolution (tens of seconds) due to slow speed of the mechanically spinning wheel for swapping filters. A multi-aperture spectral imaging system breaks through the limitation by adopting multiple color cameras equipped with multi-band bandpass optical filters and acquires MSI images through an unmixing algorithm, with a temporal resolution (<100 milliseconds, so called snapshot). However, such a system may still be affected by complexity in disparity correction of the multiple apertures.

SUMMARY

The multi-spectral imaging systems and techniques disclosed herein have several features, no single one of which is solely responsible for its desirable attributes. Without limiting the scope as expressed by the claims that follow, certain features of the disclosed spectral imaging will now be discussed briefly. One skilled in the art will understand how the features of the disclosed spectral imaging provide several advantages over traditional systems and methods.

In a first aspect of the present technology, a multispectral image system comprises a light source configured to illuminate an object by selectively emitting light comprising one or more wavebands of a set of four or more predetermined wavebands; an image sensor configured to receive a reflected portion of the emitted light that is reflected by the object; an aperture positioned to allow the reflected portion of the emitted light to pass to the image sensor; a multi-bandpass filter positioned over the aperture, wherein the multi-bandpass filter is configured to allow passage of light in the four or more predetermined wavebands; a memory storing instructions for generating and unmixing multispectral images; and at least one processor. The at least one processor is configured by the instructions to at least cause the light source to emit light of a first subset of two or more of the predetermined wavebands; receive, from the image sensor, first image data generated based on reflected light of the first subset; cause the light source to emit light of a second subset of two or more of the predetermined wavebands; receive, from the image sensor, second image data generated based on reflected light of the second subset; process the first image data and the second image data to generate at least a first multispectral image and a second multispectral image; and perform spectral unmixing to generate a plurality of single-waveband images of the object, each single-waveband image corresponding to one of the four or more predetermined wavebands.

In some embodiments, the processor is further configured to cause the light source to emit light of a third or higher ordered subset of two or more of the predetermined wavebands; and receive, from the image sensor, third or higher ordered image data generated based on reflected light of the third or higher ordered subset.

In some embodiments, the light source comprises a plurality of light emitting diodes (LEDs), each LED configured to emit light at one of the four or more predetermined wavebands. In some embodiments, the at least one processor is further configured to control activation of individual LEDs of the light source to select the wavebands simultaneously emitted by the light source. In some embodiments, the processor controls activation of the individual LEDs by controlling an electronic switching shutter to selectively pass or block the light emitted by each individual LED.

In some embodiments, the multi-bandpass filter comprises a plurality of wavebands that allow passage of light, each of the wavebands corresponding to one of the four or more predetermined wavebands. In some embodiments, the LEDs and the multi-bandpass filter comprise an equivalent number of wavebands, wherein each waveband in the LEDs aligns with a corresponding waveband in the multi-bandpass filter. In some embodiments, the multispectral image system further comprising bandpass filters positioned over individual LEDs of the plurality of LEDs to provide precise spectral confinement of the light emitted by the individual LEDs. In some embodiments, the set of four or more predetermined wavebands comprises eight predetermined wavebands, and wherein the light source comprises eight LEDs, each LED configured to emit light at one of the predetermined wavebands. In some embodiments, the multi-bandpass filter comprises an octa-band filter configured to pass each of the eight predetermined wavebands. In some embodiments, the at least one processor is further configured by the instructions to cause the light source to emit light of a third subset of the predetermined wavebands and to receive, from the image sensor, third image data generated based on reflected light of the third subset. In some embodiments, the first, second, and third subsets each comprise three of the predetermined wavebands. In some embodiments, the predetermined wavebands are defined by central wavelengths ranging from ultraviolet (UV) to short wave infrared. In some embodiments, the predetermined wavebands have central wavelengths of 420 nm, 525 nm, 581 nm, 620 nm, 660 nm, 726 nm, 820 nm, and 855 nm, respectively.

In some embodiments, the multispectral image system further comprises a parfocal or varifocal zoom lens positioned over the aperture, the one or more processors further configured to control the motorized zoom lens to adjust a field of view (FOV) of the multispectral image system. In some embodiments, the parfocal or varifocal zoom lens is configured for automatic or manual adjustment of focus by changing a focal length (FL) of the lens. In some embodiments, adjusting the FOV of the multispectral image system does not affect an object distance between the object and the image sensor. In some embodiments, the one or more processors are further configured to adjust the FOV of the multispectral image system by changing an object distance between the object and the image sensor. In some embodiments, the processor is further configured to compensate for contrast lost through the zoom lens. In some embodiments, the FOV is adjustable over at least a range of 8 cm to 23 cm e.g., 8, 9, 10, 11, 12, 13, 14, 15, 16, 17, 18, 19, 20, 21, 22, or 23 cm or within a range defined by any two of the aforementioned lengths. In some embodiments, the system retains high spatial resolution by without reducing sampling numbers in the FOV, which is different from a digital cropping method by post-processing where resolution is sacrificed.

In some embodiments, the one or more processors are further configured to generate a natural pseudocolor visualization of the object based on the multispectral images.

In some embodiments, the one or more processors are configured to perform the spectral unmixing by solving for reflectance coefficients of the object using a matrix operation equation. In some embodiments, the reflectance coefficients are determined based at least in part on channel-specific values of bare illumination intensity, transmission coefficients of the multi-bandpass filter, and quantum coefficients of the image sensor. In some embodiments, the multispectral image system is capable of capturing three or more multispectral images in less than 100 milliseconds.

In some embodiments, the object is a tissue region. In some embodiments, the tissue comprises a wound. In some embodiments, the wound comprises a diabetic ulcer, a non-diabetic ulcer, a chronic ulcer, a post-surgical incision, an amputation site, a burn, a cancerous lesion, or damaged tissue. In some embodiments, the multispectral image system is for use in identifying a tissue classification such as living or healthy tissue, dead or necrotic tissue, perfused tissue or non-perfused tissue, ischemic or non-ischemic tissue or for use in identifying a healing score of a tissue, such as a proclivity to heal by at least 50% after 30 days with standard of care therapy or a proclivity to not heal by at least 50% after 30 days with standard of care therapy. In some embodiments, the multispectral image system is for use in imaging a wound, a cancer, an ulcer, or a burn, such as a diabetic ulcer, a non-diabetic ulcer, a chronic ulcer, a post-surgical incision, an amputation site, a burn, a cancerous lesion, or damaged tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1B:
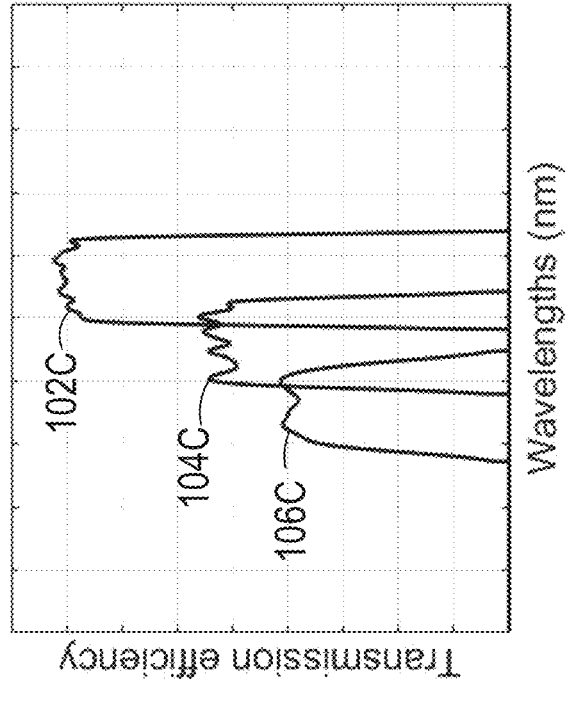
FIG. 1B is a graph illustrating example transmission efficiencies provided by the filter of FIG. 1A for various chief ray angles.

Generally described, the present disclosure relates to 2-dimensional multi-spectral imaging (MSI) using a single-aperture, single-lens, single-camera system, with features of high image acquisition speed (snapshot, <100 milliseconds), high precision of spectrum, and adjustable FOVs. The present disclosure further relates to techniques for implementing spectral unmixing to enhance acquisition speed from such systems. The disclosed technology addresses challenges present in current spectral imaging, as described below.

Multiplexed illumination based multispectral imaging can separate the spectral bands and provides fast switching capability, robustness, and cost-effectiveness. Currently, this solution adopts multiplexed illuminations with overlapped spectrums and limited channels. It best recovers the spectral reflectance $s(\lambda)$ in scenarios that $s(\lambda)$ is smooth and can be well-approximated. However, in biomedical applications, $s(\lambda)$ of biological tissue is rather complicated and high-precision spectral information is desirable. To solve the limitation, the spectral cross-talks should be significantly reduced.

The systems and methods for a high-precision snapshot multi-spectral imaging based on multiplexed illumination disclosed herein have several features. In some embodiments, the system adopts a single aperture, single lens, and single RGB color camera for 2-dimensional multi-spectral sensing. In some embodiments, the system adopts a multi-band optical filter for multi-spectral filtering. In this design, it may be, for example, an octa-band filter for 8-band MSI. However, the systems and methods disclosed herein are not limited to the numbers specified in the present disclosure, and may equally be applied with more or fewer wavelength bands for MSI. In some embodiments, the system adopts 8 wavelengths of light-emitting diodes (LED) for illumination, each wavelength spectrum overlaying with each MSI band. In some embodiments, each LED has a band-pass optical filter placed at its front with a matched MSI band. In some embodiments, the system adopts a motorized zoom lens. Spectrum-unmixing methods may be used to accelerate imaging speed, through modulation of LED illumination. Multiple wavelengths of LEDs can be turned on and off in particular combinations and time sequences, as will be discussed in greater detail. Unmixing coefficients may be calculated based on LED illumination intensity ($I_0$), filter transmission coefficients (T %), and/or color camera RGB channel sensing quantum efficiency (Q %).

Various embodiments of the systems and methods of the present disclosure can provide multi-spectral imaging with improved features including but not limited to one or more of: (a) no complicated algorithms in disparity correction and no disparity error, by adopting a single aperture system; (b) smaller form factors (e.g., smaller volumes and weights) and lower costs, in comparison to the multi-aperture systems; (c) high image acquisition speed (<100 milliseconds) and fast post-processing speed, thus less motion artifacts and feasibility in real-time imaging; (d) high precision of spectral information, confined by the narrow-band LED illumination, band-pass optical filters in front of LEDs, and the multi-band optical filter; (e) adjustable FOVs for different applications, through the motorized zoom lens; (f) a natural pseudocolor visualization based on MSI images; (g) capability of multi-functional biomedical imaging.

Compared to the FilterWheel based single-aperture multi-spectral imaging system, which includes a mechanically spinning filter wheel, the present system may provide high acquisition speed with an octa-band filter for multi-bandpass optical filtering. Meanwhile, in some embodiments, each MSI band (e.g., channel) spectral information is retrieved by adopting multi-color LEDs whose spectrums closely or precisely overlaps with the desired MSI bands. The precise spectrum of illumination, along with the spectral confinement by LED filters and the octa-band filter, avoids out-of-band leakage and cross-talk between channels, and significantly enhances spectral precision. Each LED can be turned on and off quickly and repetitively so that single-color illuminations can be achieved by using time-gated sequences.

In some embodiments, the system can work in an ambient or room light environment by acquiring a background image (e.g., without any LED illumination); the background image can then be subtracted from acquired MSI images (e.g., which are exposed to LED illumination plus room light). Furthermore, the MSI acquisition speed may be further enhanced in some embodiments by adopting a multi-channel imaging sensor (e.g., RGB camera) such that 3 channels of LEDs can be turned on at the same time and the spectral information from the 3 channels can be separated through an unmixing algorithm. The snapshot imaging speed presented in this disclosed technology can accordingly provide much faster imaging and significantly reduce target motion artifacts and will benefit in many biomedical applications.

Compared to a multi-aperture MSI imaging system, the present systems and methods can adopt a single-aperture, single-lens, single-camera configuration in some embodiments so that the system does not require disparity correction calculations which may require complicated algorithms that can significantly slow image post-processing speed. Additionally, the implementation of a single-aperture, single-lens, single-camera configuration may avoid misinterpretation in pixel-based spectral information. For example, existing multi-aperture MSI imaging systems can separate spectral bands through separation of imaging sensors (e.g., a multiple camera configuration) and unmixing algorithms. Systems and methods of the present disclosure can separate spectral bands through multiplexed illumination (e.g., independently-controlled multi-color LEDs), as well as an unmixing algorithm. Because the LED illumination operation time sequences are controlled through an electronic switching shutter, which is much faster than a mechanical spinning wheel containing individual single-band bandpass filters in the FilterWheel system, the present disclosure provides an instant band-swapping and its imaging acquisition speed is close to that of a multi-aperture MSI imaging system, while avoiding the need for disparity correction calculation and with fast post-processing.

The systems and methods of the present disclosure can use band-pass optical filters for LED illumination and an octa-band optical filter on the detector side, and thus can greatly confine the sensing spectrum in desired bands, avoid cross-talk between each illumination, remove out-of-band leakage, and enhance the spectral precision. The present disclosure provides the benefits with a simple design which improves over existing systems that include multiplexed illumination.

Overview of Spectral Imaging Systems

Figure 1A:
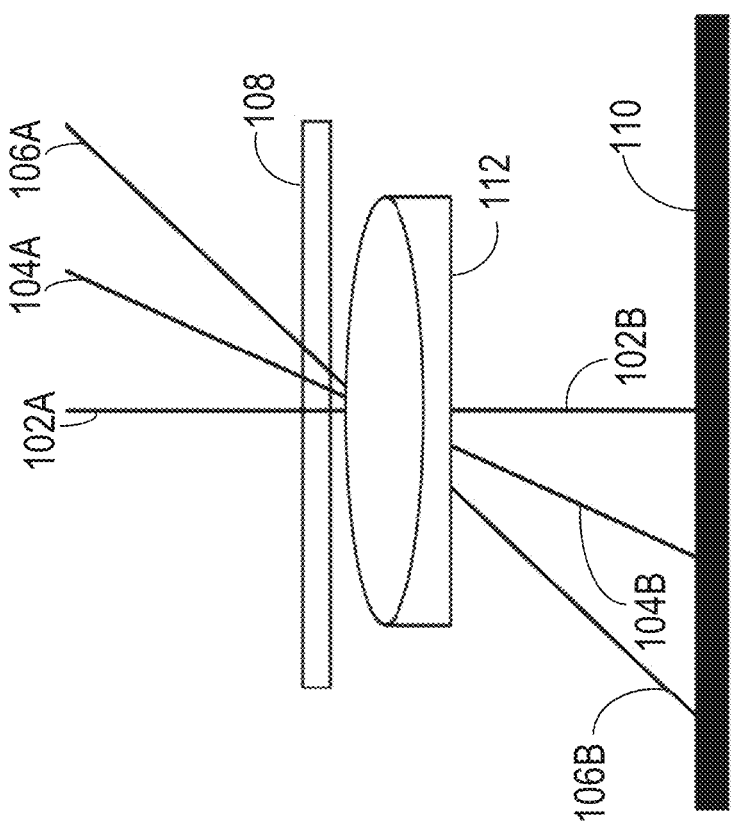
FIG. 1A illustrates an example of light incident on a filter at different chief ray angles.

FIG. 1A illustrates an example of a filter 108 positioned along the path of light towards an image sensor 110, and also illustrates light incident on the filter 108 at different ray angles. The rays 102A, 104A, 106A are represented as lines which, after passing through the filter 108, are refracted onto the sensor 110 by a lens 112, which may also be substituted with any other image-forming optics, including but not limited to a mirror and/or an aperture. The light for each ray is presumed in FIG. 1A to be broadband, for example, having a spectral composition extending over a large wavelength range to be selectively filtered by filter 108. The three rays 102A, 104A, 106A each arrive at the filter 108 at a different angle. For illustrative purposes, light ray 102A is shown as being incident substantially normal to filter 108, light ray 104A has a greater angle of incidence than light ray 102A, and light ray 106A has a greater angle of incidence than light ray 104A. The resulting filtered rays 102B, 104B, 106B exhibit a unique spectrum due to the angular dependence of the transmittance properties of the filter 108 as seen by the sensor 110. The effect of this dependence causes a shift in the bandpass of the filter 108 towards shorter wavelengths as the angle of incidence increases. Additionally, the dependence may cause a reduction in the transmission efficiency of the filter 108 and an altering of the spectral shape of the bandpass of the filter 108. These combined effects are referred to as the angular-dependent spectral transmission. FIG. 1B depicts the spectrum of each light ray in FIG. 1A as seen by a hypothetical spectrometer at the location of sensor 110 to illustrate the shifting of the spectral bandpass of filter 108 in response to increasing angle of incidence. The curves 102C, 104C, and 106C demonstrate the shortening of the center wavelength of the bandpass; hence, the shortening of the wavelengths of light passed by the optical system in the example. Also shown, the shape of the bandpass and the peak transmission are altered due to the angle incidence as well. For certain consumer applications, image processing can be applied to remove the visible effects of this angular-dependent spectral transmission. However, these post-processing techniques do not allow for recovery of precise information regarding which wavelength of light was actually incident upon the filter 108. Accordingly, the resulting image data may be unusable for certain high-precision applications.

Figure 2A:
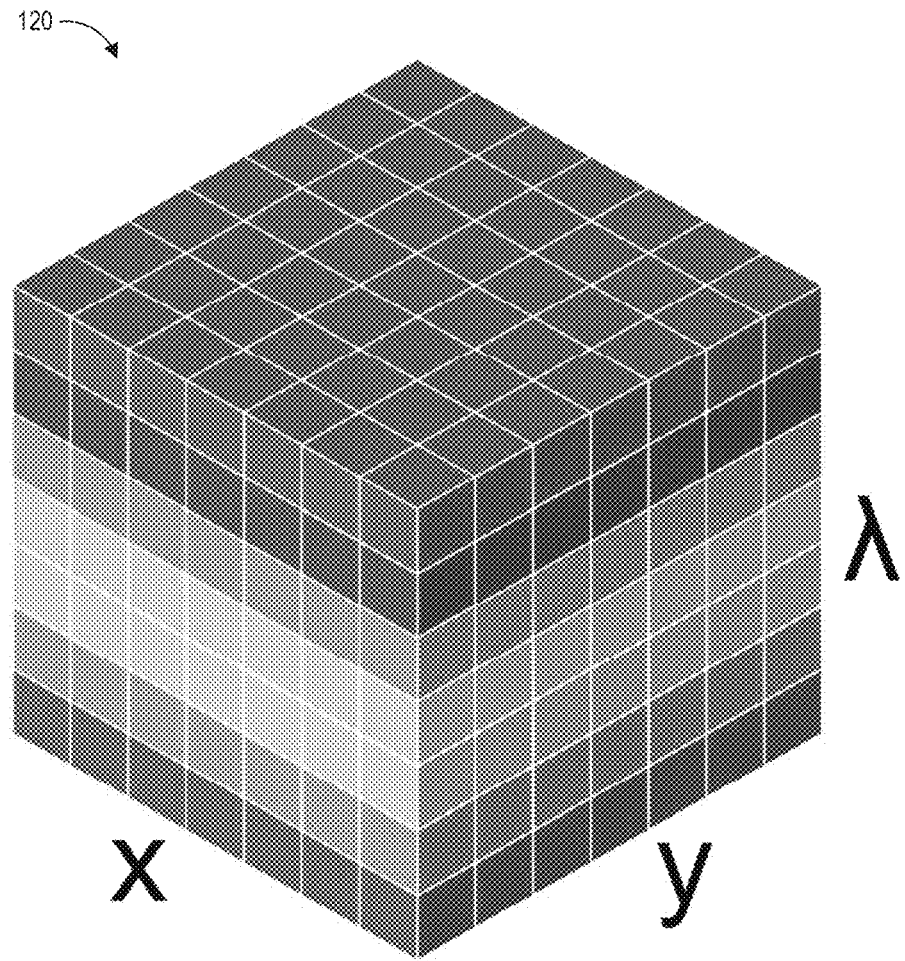
FIG. 2A illustrates an example of a multispectral image datacube.

Another challenge faced by certain existing spectral imaging systems is the time required for capture of a complete set of spectral image data, as discussed in connection with FIGS. 2A and 2B. Spectral imaging sensors sample the spectral irradiance $I(x, y, \lambda)$ of a scene and thus collect a three-dimensional (3D) dataset typically called a datacube. FIG. 2A illustrates an example of a spectral image datacube 120. As illustrated, the datacube 120 represents three dimensions of image data: two spatial dimensions (x and y) corresponding to the two-dimensional (2D) surface of the image sensor, and a spectral dimension ($\lambda$) corresponding to a particular wavelength band. The dimensions of the datacube 120 can be given by $N_x N_y N_\lambda$, where $N_x$, $N_y$, and $N_\lambda$ are the number of sample elements along the (x, y) spatial dimensions and spectral axes A, respectively. Because datacubes are of a higher dimensionality than 2D detector arrays (e.g., image sensors) that are currently available, typical spectral imaging systems either capture time-sequential 2D slices, or planes, of the datacube 120 (referred to herein as "scanning" imaging systems), or simultaneously measure all elements of the datacube by dividing it into multiple 2D elements that can be recombined into datacube 120 in processing (referred to herein as "snapshot" imaging systems).

Figure 2B:
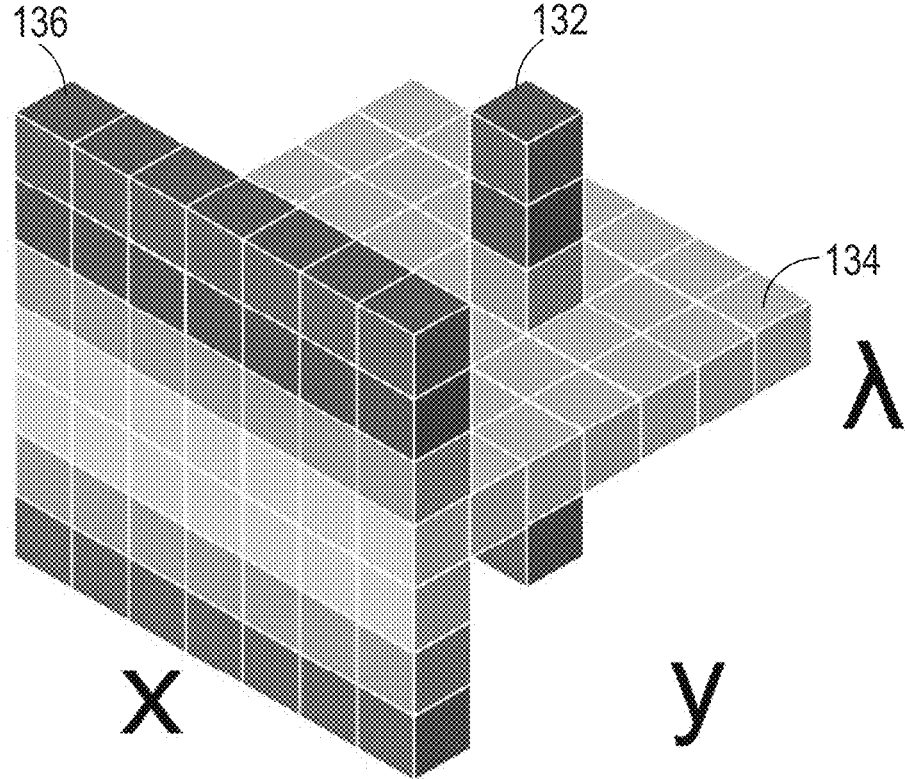
FIG. 2B illustrates examples of how certain multispectral imaging technologies generate the datacube of FIG. 2A.

FIG. 2B illustrates examples of how certain scanning spectral imaging technologies generate the datacube 120. Specifically, FIG. 2B illustrates the portions 132, 134, and 136 of the datacube 120 that can be collected during a single detector integration period. A point scanning spectrometer, for example, can capture a portion 132 that extends across all spectral planes A at a single (x, y) spatial position. A point scanning spectrometer can be used to build the datacube 120 by performing a number of integrations corresponding to each (x, y) position across the spatial dimensions. A filter wheel imaging system, for example, can capture a portion 134 that extends across the entirety of both spatial dimensions x and y, but only a single spectral plane $\lambda$. A wavelength scanning imaging system, such as a filter wheel imaging system, can be used to build the datacube 120 by performing a number of integrations corresponding to the number of spectral planes $\lambda$. A line scanning spectrometer, for example, can capture a portion 136 that extends across all spectral dimensions A and all of one of the spatial dimension (x or y), but only a single point along the other spatial dimension (y or x). A line scanning spectrometer can be used to build the datacube 120 by performing a number of integrations corresponding to each position of this other spatial dimension (y or x).

For applications in which the target object and imaging system are both motionless (or remain relatively still over the exposure times), such scanning imaging systems provide the benefit of yielding a high resolution datacube 120. For line scanning and wavelength scanning imaging systems, this can be due to the fact that each spectral or spatial image is captured using the entire area of the image sensor. However, movement of the imaging system and/or object between exposures can cause artifacts in the resulting image data. For example, the same (x, y) position in the datacube 120 can actually represent a different physical location on the imaged object across the spectral dimension $\lambda$. This can lead to errors in downstream analysis and/or impose an additional requirement for performing registration (e.g., aligning the spectral dimension $\lambda$ so that a particular (x, y) position corresponds to the same physical location on the object).

Figure 2C:
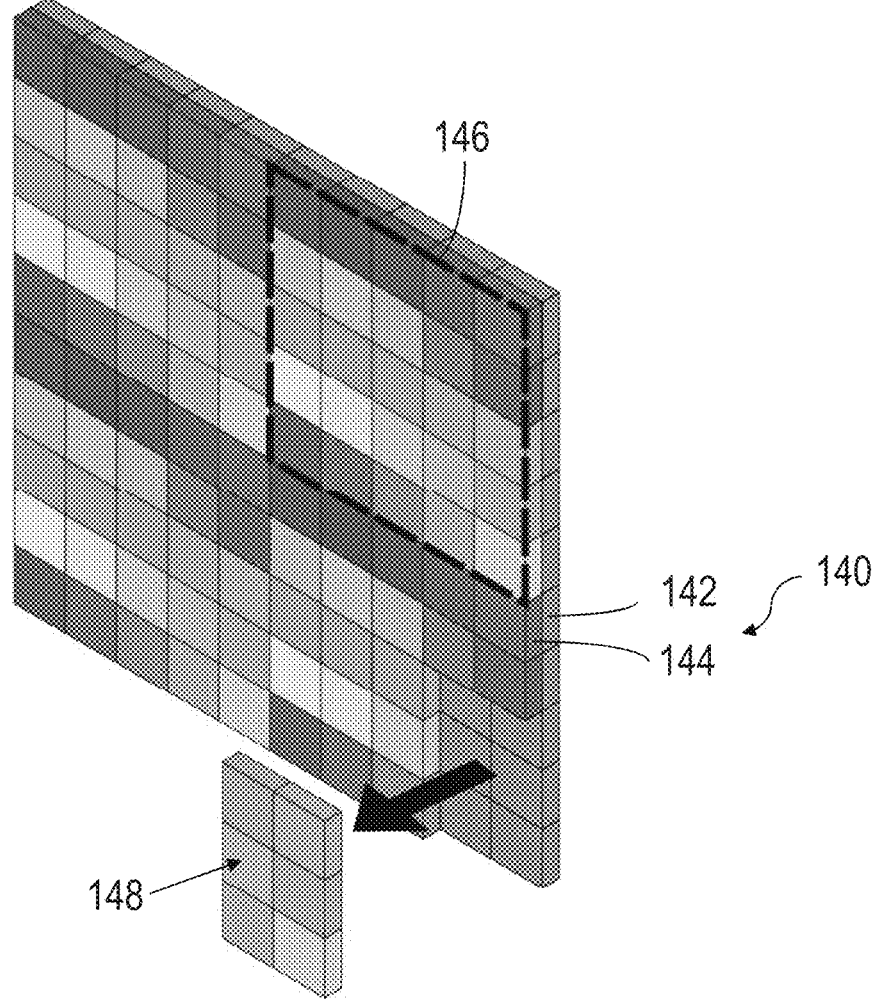
FIG. 2C depicts an example snapshot imaging system that can generate the datacube of FIG. 2A.

In comparison, a snapshot imaging system 140 can capture an entire datacube 120 in a single integration period or exposure, thereby avoiding such motion-induced image quality issues. FIG. 2C depicts an example image sensor 142 and an optical filter array such as a color filter array (CFA) 144 that can be used to create a snapshot imaging system. The CFA 144 in this example is a repeating pattern of color filter units 146 across the surface of the image sensor 142. This method of acquiring spectral information can also be referred to as a multispectral filter array (MSFA) or a spectrally resolved detector array (SRDA). In the illustrated example, the color filter unit 146 includes a 5×5 arrangement of different color filters, which would generate 25 spectral channels in the resulting image data. By way of these different color filters, the CFA can split incoming light into the bands of the filters, and direct the split light to dedicated photoreceptors on the image sensor. In this way, for a given color 148, only $\frac{1}{25}^{th}$ of the photoreceptors actually detect a signal represent light of that wavelength. Thus, although 25 different color channels can be generated in a single exposure with this snapshot imaging system 140, each color channel represents a smaller quantity of measured data than the total output of the sensor 142. In some embodiments, a CFA may include one or more of a filter array (MSFA), a spectrally resolved detector array (SRDA), and/or may include a conventional Bayer filter, CMYK filter, or any other absorption-based or interference-based filters. One type of interference based filter would be an array of thin film filters arranged in a grid with each element of the grid corresponding to one or more sensor elements. Another type of interference based filter is a Fabry-Perot filter. Nano-etched interference Fabry-Perot filters, which exhibit typical bandpass full-width-at-half-maxima (FWHM) on the order of 20 to 50 nm (e.g., 20, 21, 22, 23, 24, 25, 26, 27, 28, 29, 30, 31, 32, 33, 34, 35, 36, 37, 38, 39, 40, 41, 52, 53, 44, 45, 46, 47, 48, 49, or 50 nm or of a length defined by a range composed of any two of the aforementioned lengths), are advantageous because they can be used in some embodiments due to the slow roll-off of the filters' passband seen in the transition from its center wavelength to its blocking band. These filters also exhibit a low OD in these blocking bands further enabling increased sensitivity to light outside of their passbands. These combined effects makes these specific filters sensitive to spectral regions that would otherwise be blocked by the fast roll-off of a high OD interference filter with a similar FWHM made with many thin film layers in a coating deposition process such as in evaporative deposition or in ion-beam sputtering. In embodiments with dye-based CMYK or RGB (Bayer) filter configurations, the slow spectral roll-off and the large FWHM of individual filter passbands are preferred and provide a unique spectral transmission percentage to individual wavelengths throughout an observed spectrum.

Accordingly, the datacube 120 that results from a snapshot imaging system will have one of two properties that can be problematic for precision imaging applications. As a first option, the datacube 120 that results from a snapshot imaging system can have smaller $N_x$ and $N_y$ sizes than the (x, y) size of the detector array and, thus be of lower resolution than the datacube 120, which would be generated by a scanning imaging system having the same image sensor. As a second option, the datacube 120 that results from a snapshot imaging system can have the same $N_x$ and $N_y$ sizes as the (x, y) size of the detector array due to interpolating values for certain (x, y) positions. However, the interpolation used to generate such a datacube means that certain values in the datacube are not actual measurements of the wavelength of light incident on the sensor, but rather estimates of what the actual measurement may be based on surrounding values.

Another existing option for single-exposure multispectral imaging is the multispectral beamsplitter. In such imaging systems, beamsplitter cubes split incident light into distinct color bands, with each band observed by independent image sensors. While one can change the beamsplitter designs to adjust the measured spectral bands, it is not easy to divide the incident light into more than four beams without compromising the system performance. Thus, four spectral channels appear to be the practical limit of this approach. A closely related method is to use thin-film filters instead of the bulkier beamsplitter cubes/prisms to split the light, however this approach is still limited to about six spectral channels due to space limitations and cumulative transmission losses through successive filters.

The aforementioned problems, among others, are addressed in some embodiments by the disclosed spectral imaging system with multiplexed illumination, multi-bandpass filters to filter illumination light, and the use of color channels of an RGB camera, as well as the associated image data processing techniques. This particular configuration is able to achieve all of the design goals of fast imaging speeds, high resolution images, and precise fidelity of detected wavelengths. Accordingly, the disclosed optical design and associated image data processing techniques can be used in portable spectral imaging systems and/or to image moving targets, while still yielding a datacube suitable for high precision applications (e.g., clinical tissue analysis, biometric recognition, transient clinical events). These higher precision applications, which can be accomplished utilizing one or more of the embodiments described herein, may include the diagnosis of basal cell carcinomas, squamous cell carcinomas, and melanomas in the preceeding stages (0 through 3) before metastasis, the classification of burn or wound severity on a skin tissue, the identification and margins of necrotic or ischemic tissue e.g., as contrasted with healthy or normal skin, or the tissue diagnosis or severity of peripheral vascular disease or diabetic foot ulcers. Accordingly, the small form factor and the snapshot spectral acquisition as depicted in some embodiments will enable the use of this invention in clinical environments with transient events, which include e.g., the diagnosis of several different retinopathies (e.g. non proliferative diabetic retinopathy, proliferative diabetic retinopathy, and age-related macular degeneration) and the imaging of moving pediatric patients.

Accordingly, it will be appreciated by one of skill in the art that the use of a system as disclosed herein represents a significant technological advance over prior spectral imaging implementations.

Various aspects of the disclosure will now be described with regard to certain examples and embodiments, which are intended to illustrate but not limit the disclosure. Although the examples and embodiments described herein will focus, for the purpose of illustration, on specific calculations and algorithms, one of skill in the art will appreciate the examples are to illustrate only, and are not intended to be limiting. For example, although some examples are presented in the context of multispectral imaging, the disclosed single-aperture imaging system and associated filters and multiplexed illumination can be configured to achieve hyperspectral imaging in other implementations. Further, although certain examples are presented as achieving benefits for handheld and/or moving target applications, it will be appreciated that the disclosed imaging system designs and associated processing techniques can yield a high precision datacube suitable for fixed imaging systems and/or for analysis of relatively motionless targets.

Overview of Electromagnetic Ranges and Image Sensors

Certain colors or portions of the electromagnetic spectrum are referred to herein, and will now be discussed with respect to their wavelength as defined by the ISO 21348 definitions of irradiance spectral categories. As described further below, in certain imaging applications the wavelength ranges for specific colors can be grouped together to pass through a certain filter.

Electromagnetic radiation ranging from wavelengths of or approximately 760 nm to wavelengths of or approximately 380 nm are typically considered the "visible" spectrum, that is, the portion of the spectrum recognizable by the color receptors of the human eye. Within the visible spectrum, red light typically is considered to have a wavelength of or approximately 700 nanometers (nm), or to be in the range of or approximately 760 nm to 610 nm or approximately 610 nm. Orange light typically is considered to have a wavelength of or approximately 600 nm, or to be in the range of or approximately 610 nm to approximately 591 nm or 591 nm. Yellow light typically is considered to have a wavelength of or approximately 580 nm, or to be in the range of or approximately 591 nm to approximately 570 nm or 570 nm. Green light typically is considered to have a wavelength of or approximately 550 nm, or to be in the range of or approximately 570 nm to approximately 500 nm or 500 nm. Blue light typically is considered to have a wavelength of or approximately 475 nm, or to be in the range of or approximately 500 nm to approximately 450 nm or 450 nm. Violet (purple) light typically is considered to have a wavelength of or approximately 400 nm, or to be in the range of or approximately 450 nm to approximately 360 nm or 360 nm.

Turning to ranges outside of the visible spectrum, infrared (IR) refers to electromagnetic radiation with longer wavelengths than those of visible light, and is generally invisible to the human eye. IR wavelengths extend from the nominal red edge of the visible spectrum at approximately 760 nm or 760 nm to approximately 1 millimeter (mm) or 1 mm. Within this range, near infrared (NIR) refers to the portion of the spectrum that is adjacent to the red range, ranging from wavelengths between approximately 760 nm or 760 nm to approximately 1400 nm or 1400 nm.

Ultraviolet (UV) radiation refers to some electromagnetic radiation with shorter wavelengths than those of visible light, and is generally invisible to the human eye. UV wavelengths extend from the nominal violet edge of the visible spectrum at approximately 40 nm or 40 nm to approximately 400 nm. Within this range, near ultraviolet (NUV) refers to the portion of the spectrum that is adjacent to the violet range, ranging from wavelengths between approximately 400 nm or 400 nm to approximately 300 nm or 300 nm, middle ultraviolet (MUV) ranges from wavelengths between approximately 300 nm or 300 nm to approximately 200 nm or 200 nm, and far ultraviolet (FUV) ranges from wavelengths between approximately 200 nm or 200 nm to approximately 122 nm or 122 nm.

The image sensors described herein can be configured to detect electromagnetic radiation in any of the above-described ranges, depending upon the particular wavelength ranges that are suitable for a particular application. The spectral sensitivity of a typical silicon-based charge-coupled device (CCD) or complementary metal-oxide-semiconductor (CMOS) sensor extends across the visible spectrum, and also extends considerably into the near-infrared (IR) spectrum and sometimes into the UV spectrum. Some implementations can alternatively or additionally use back-illuminated or front-illuminated CCD or CMOS arrays. For applications requiring high SNR and scientific-grade measurements, some implementations can alternatively or additionally use either scientific complementary metal-oxide-semiconductor (sCMOS) cameras or electron multiplying CCD cameras (EMCCD). Other implementations can alternatively or additionally use sensors known to operate in specific color ranges (e.g., short-wave infrared (SWIR), mid-wave infrared (MWIR), or long-wave infrared (LWIR)) and corresponding optical filter arrays, based on the intended applications. These may alternatively or additionally include cameras based around detector materials including indium gallium arsenide (InGaAs) or indium antimonide (InSb) or based around microbolometer arrays.

The image sensors used in the disclosed multispectral imaging techniques may be used in conjunction with an optical filter array such as a color filter array (CFA). Some CFAs can split incoming light in the visible range into red (R), green (G), and blue (B) categories to direct the split visible light to dedicated red, green, or blue photodiode receptors on the image sensor. A common example for a CFA is the Bayer pattern, which is a specific pattern for arranging RGB color filters on a rectangular grid of photosensors. The Bayer pattern is 50% green, 25% red and 25% blue with rows of repeating red and green color filters alternating with rows of repeating blue and green color filters. Some CFAs (e.g., for RGB-NIR sensors) can also separate out the NIR light and direct the split NIR light to dedicated photodiode receptors on the image sensor.

As such, the wavelength ranges of the filter components of the CFA can determine the wavelength ranges represented by each image channel in a captured image. Accordingly, a red channel of an image may correspond to the red wavelength regions of the color filter and can include some yellow and orange light, ranging from approximately 570 nm or 570 nm to approximately 760 nm or 760 nm in various embodiments. A green channel of an image may correspond to a green wavelength region of a color filter and can include some yellow light, ranging from approximately 570 nm or 570 nm to approximately 480 nm or 480 nm in various embodiments. A blue channel of an image may correspond to a blue wavelength region of a color filter and can include some violet light, ranging from approximately 490 nm or 490 nm to approximately 400 nm or 400 nm in various embodiments. As a person of ordinary skill in the art will appreciate, exact beginning and ending wavelengths (or portions of the electromagnetic spectrum) that define colors of a CFA (for example, red, green, and blue) can vary depending upon the CFA implementation.

Further, typical visible light CFAs are transparent to light outside the visible spectrum. Therefore, in many image sensors the IR sensitivity is limited by a thin-film reflective IR filter at the face of the sensor that blocks the infrared wavelength while passing visible light. However, this may be omitted in some of the disclosed imaging systems to allow of passage of IR light. Thus, the red, green, and/or blue channels may also be used to collect IR wavelength bands. In some implementations the blue channel may also be used to collect certain NUV wavelength bands. The distinct spectral responses of the red, green, and blue channels with regard to their unique transmission efficiencies at each wavelength in a spectral image stack may provide a uniquely weighted response of spectral bands to be unmixed using the known transmission profiles. For example, this may include the known transmission response in IR and UV wavelength regions for the red, blue, and green channels, enabling their use in the collection of bands from these regions.

As described in further detail below, additional color filters can be placed before the CFA along the path of light towards the image sensor in order to selectively refine the specific bands of light that become incident on the image sensor. Some of the disclosed filters can be either a combination of dichroic (thin-film) and/or absorptive filters or a single dichroic and/or absorptive filter. Some of the disclosed color filters can be bandpass filters that pass frequencies within a certain range (in a passband) and reject (attenuates) frequencies outside that range (in a blocking range). Some of the disclosed color filters can be multi-bandpass filters that pass multiple discontinuous ranges of wavelengths. These "wavebands" can have smaller passband ranges, larger blocking range attenuation, and sharper spectral roll-off, which is defined as the steepness of the spectral response as the filter transitions from the passband to the blocking range, than the larger color range of the CFA filter. For example, these disclosed color filters can cover a passband of approximately 20 nm or 20 nm or approximately 40 nm or 40 nm. The particular configuration of such color filters can determine the actual wavelength bands that are incident upon the sensor, which can increase the precision of the disclosed imaging techniques. The color filters described herein can be configured to selectively block or pass specific bands of electromagnetic radiation in any of the above-described ranges, depending upon the particular wavelength bands that are suitable for a particular application.

As described herein, a "pixel" can be used to describe the output generated by an element of the 2D detector array. In comparison, a photodiode, a single photosensitive element in this array, behaves as a transducer capable of converting photons into electrons via the photoelectric effect, which is then in turn converted into a usable signal used to determine the pixel value. A single element of the datacube can be referred to as a "voxel" (e.g., a volume element). A "spectral vector" refers to a vector describing the spectral data at a particular (x, y) position in a datacube (e.g., the spectrum of light received from a particular point in the object space). A single horizontal plane of the datacube (e.g., an image representing a single spectral dimension), is referred to herein as a an "image channel". Certain embodiments described herein may capture spectral video information, and the resulting data dimensions can assume the "hypercube" form $N_x N_y N_\lambda N_t$, where $N_t$ is the number of frames captured during a video sequence.

Overview of Example Imaging Systems

Figure 3A:
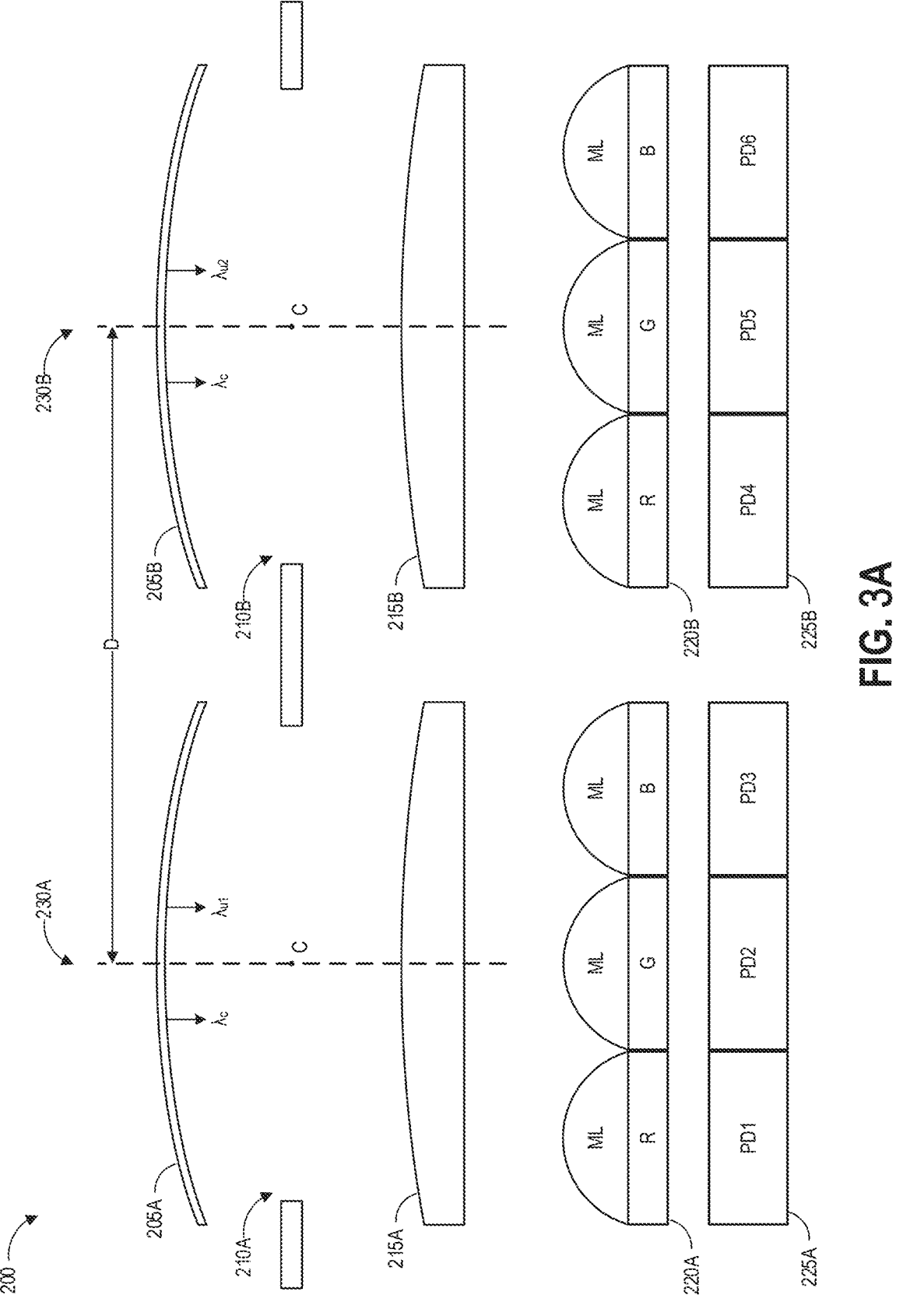
FIG. 3A depicts a schematic cross-sectional view of an optical design of an example multi-aperture imaging system with curved multi-bandpass filters, according to the present disclosure.

FIG. 3A depicts a schematic view of an example multi-aperture imaging system 200 with curved multi-bandpass filters, according to the present disclosure. The illustrated view includes a first image sensor region 225A (photodiodes PD1-PD3) and a second image sensor region 225B (photodiodes PD4-PD6). The photodiodes PD1-PD6 can be, for example, photodiodes formed in a semiconductor substrate, for example in a CMOS image sensor. Generally, each of the photodiodes PD1-PD6 can be a single unit of any material, semiconductor, sensor element or other device that converts incident light into current. It will be appreciated that a small portion of the overall system is illustrated for the purpose of explaining its structure and operation, and that in implementation image sensor regions can have hundreds or thousands of photodiodes (and corresponding color filters). The image sensor regions 225A and 225B may be implemented as separate sensors, or as separate regions of the same image sensor, depending upon the implementation. Although FIG. 3A depicts two apertures and corresponding light paths and sensor regions, it will be appreciated that the optical design principles illustrated by FIG. 3A can be extended to three or more apertures and corresponding light paths and sensor regions, depending upon the implementation.

The multi-aperture imaging system 200 includes a first opening 210A that provides a first light path towards the first sensor region 225A, and a second opening 210B that provides a first light path towards the second sensor region 225B. These apertures may be adjustable to increase or decrease the brightness of the light that falls on the image, or so that the duration of particular image exposures can be changed and the brightness of the light that falls on the image sensor regions does not change. These apertures may also be located at any position along the optical axes of this multi-aperture system as deemed reasonable by one skilled in the art of optical design. The optical axis of the optical components positioned along the first light path is illustrated by dashed line 230A and the optical axis of the optical components positioned along the second light path is illustrated by dashed line 230B, and it will be appreciated that these dashed lines do not represent a physical structure of the multi-aperture imaging system 200. The optical axes 230A, 230B are separated by a distance D, which can result in disparity between the images captured by the first and second sensor regions 225A, 225B. Disparity refers to the distance between two corresponding points in the left and right (or upper and lower) images of a stereoscopic pair, such that the same physical point in the object space can appear in different locations in each image. Processing techniques to compensate for and leverage this disparity are described in further detail below.

Each optical axis 230A, 230B passes through a center C of the corresponding aperture, and the optical components can also be centered along these optical axes (e.g., the point of rotational symmetry of an optical component can be positioned along the optical axis). For example, the first curved multi-bandpass filter 205A and first imaging lens 215A can be centered along the first optical axis 230A, and the second curved multi-bandpass filter 205B and second imaging lens 215B can be centered along the second optical axis 230B.

As used herein with respect to positioning of optical elements, "over" and "above" refer to the position of a structure (for example, a color filter or lens) such that light entering the imaging system 200 from the object space propagates through the structure before it reaches (or is incident upon) another structure. To illustrate, along the first light path, the curved multi-bandpass filter 205A is positioned above the aperture 210A, the aperture 210A is positioned above imaging lens 215A, the imaging lens 215A is positioned above the CFA 220A, and the CFA 220A is positioned above the first image sensor region 225A. Accordingly, light from the object space (e.g., the physical space being imaged) first passes through the curved multi-bandpass filter 205A, then the aperture 210A, then the imaging lens 215A, then the CFA 220A, and finally is incident on the first image sensor region 225A. The second light path (e.g., curved multi-bandpass filter 205B, aperture 210B, imaging lens 215B, CFA 220B, second image sensor region 225B) follows a similar arrangement. In other implementations, the aperture 210A, 210B and/or imaging lenses 215A, 215B can be positioned above the curved multi-bandpass filter 205A, 205B. Additionally, other implementations may not use a physical aperture and may rely on the clear aperture of the optics to control the brightness of light that is imaged onto the sensor region 225A, 225B. Accordingly, the lens 215A, 215B may be placed above the aperture 210A, 210B and curved multi-bandpass filter 205A, 205B. In this implementation, the aperture 210A, 210B and lens 215A, 215B may be also be placed over or under each other as deemed necessary by one skilled in the art of optical design.

The first CFA 220A positioned over the first sensor region 225A and the second CFA 220B positioned over the second sensor region 225B can act as wavelength-selective pass filters and split incoming light in the visible range into red, green, and blue ranges (as indicated by the R, G, and B notation). The light is "split" by allowing only certain selected wavelengths to pass through each of the color filters in the first and second CFAs 220A, 220B. The split light is received by dedicated red, green, or blue diodes on the image sensor. Although red, blue, and green color filters are commonly used, in other embodiments the color filters can vary according to the color channel requirements of the captured image data, for example including ultraviolet, infrared, or near-infrared pass filters, as with an RGB-IR CFA.

As illustrated, each filter of the CFA is positioned over a single photodiode PD1-PD6. FIG. 3A also illustrates example microlenses (denoted by ML) that can be formed on or otherwise positioned over each color filter, in order to focus incoming light onto active detector regions. Other implementations may have multiple photodiodes under a single filter (e.g., clusters of 2, 4, or more adjacent photodiodes). In the illustrated example, photodiode PD1 and photodiode PD4 are under red color filters and thus would output red channel pixel information; photodiode PD2 and photodiode PD5 are under green color filters and, thus would output green channel pixel information; and photodiode PD3 and photodiode PD6 are under blue color filters and thus would output blue channel pixel information. Further, as described in more detail below, the specific color channels output by given photodiodes can be further limited to narrower wavebands based on activated illuminants and/or the specific wavebands passed by the multi-bandpass filters 205A, 205B, such that a given photodiode can output different image channel information during different exposures.

The imaging lenses 215A, 215B can be shaped to focus an image of the object scene onto the sensor regions 225A, 225B. Each imaging lens 215A, 215B may be composed of as many optical elements and surfaces needed for image formation and are not limited to single convex lenses as presented in FIG. 3A, enabling the use of a wide variety of imaging lenses or lens assemblies that would be available commercially or by custom design. Each element or lens assembly may be formed or bonded together in a stack or held in series using an optomechanical barrel with a retaining ring or bezel. In some embodiments, elements or lens assemblies may include one or more bonded lens groups, such as two or more optical components cemented or otherwise bonded together. In various embodiments, any of the multi-bandpass filters described herein may be positioned in front of a lens assembly of the multispectral image system, in front of a singlet of the multispectral image system, behind a lens assembly of the multispectral image system, behind a singlet of the multispectral image system, inside a lens assembly of the multispectral image system, inside a bonded lens group of the multispectral image system, directly onto a surface of a singlet of the multispectral image system, or directly onto a surface of an element of a lens assembly of the multispectral image system. Further, the aperture 210A and 210B may be removed, and the lenses 215A, 215B may be of the variety typically used in photography with either digital-single-lens-reflex (DSLR) or mirrorless cameras. Additionally, these lenses may be of the variety used in machine vision using C-mount or S-mount threading for mounting. Focus adjustment can be provided by movement of the imaging lenses 215A, 215B relative to the sensor regions 225A, 225B or movement of the sensor regions 225A, 225B relative to the imaging lenses 215A, 215B, for example based on manual focusing, contrast-based autofocus, or other suitable autofocus techniques.

The multi-bandpass filters 205A, 205B can be each configured to selectively pass multiple narrow wavebands of light, for example wavebands of 10-50 nm in some embodiments (or wider or narrower wavebands in other embodiments). As illustrated in FIG. 3A, both multi-bandpass filters 205A, 205B can pass waveband $\lambda_c$ (the "common waveband"). In implementations with three or more light paths, each multi-bandpass filter can pass this common waveband. In this manner, each sensor region captures image information at the same waveband (the "common channel"). This image information in this common channel can be used to register the sets of images captured by each sensor region, as described in further detail below. Some implementations may have one common waveband and corresponding common channel, or may have multiple common wavebands and corresponding common channels.

In addition to the common waveband $\lambda_c$, each multi-bandpass filters 205A, 205B can be each configured to selectively pass one or more unique wavebands. In this manner, the imaging system 200 is able to increase the number of distinct spectral channels captured collectively by the sensor regions 205A, 205B beyond what can be captured by a single sensor region. This is illustrated in FIG. 3A by multi-bandpass filters 205A passing unique waveband $\lambda_{u1}$, and multi-bandpass filters 205B passing unique waveband $\lambda_{u2}$, where $\lambda_{u1}$ and $\lambda_{u2}$ represent different wavebands from one another. Although depicted as passing two wavebands, the disclosed multi-bandpass can each pass a set of two or more wavebands. For example, some implementations can pass four wavebands each, as described with respect to FIGS. 11A and 11B. In various embodiments, a larger number of wavebands may be passed. For example, some four-camera implementations may include multi-bandpass filters configured to pass 8 wavebands. In some embodiments, the number of wavebands may be, for example, 4, 5, 6, 7, 8, 9, 10, 12, 15, 16, or more wavebands.

The multi-bandpass filters 205A, 205B have a curvature selected to reduce the angular-dependent spectral transmission across the respective sensor regions 225A, 225B. As a result, when receiving narrowband illumination from the object space, each photodiode across the area of the sensor regions 225A, 225B that is sensitive to that wavelength (e.g., the overlying color filter passes that wavelength) should receive substantially the same wavelength of light, rather than photodiodes near the edge of the sensor experiencing the wavelength shift described above with respect to FIG. 1A. This can generate more precise spectral image data than using flat filters.

Figure 3B:
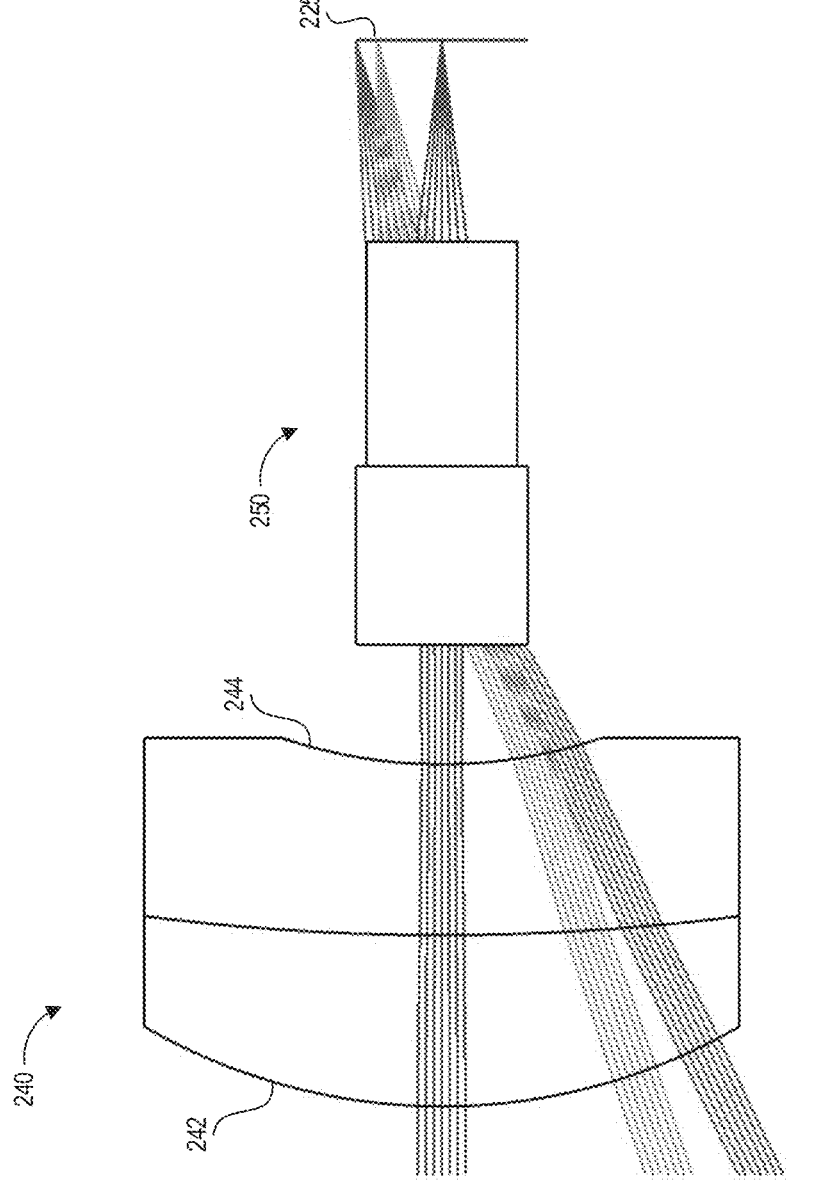
FIGS. 3B-3D depict example optical designs for optical components of one light path of the multi-aperture imaging system of FIG. 3A.

FIG. 3B depicts an example optical design for optical components of one light path of the multi-aperture imaging system of FIG. 3A. Specifically, FIG. 3B depicts a custom achromatic doublet 240 that can be used to provide the multi-bandpass filters 205A, 205B. The custom achromatic doublet 240 passes light through a housing 250 to an image sensor 225. The housing 250 can include openings 210A, 210B and imaging lens 215A, 215B described above.

The achromatic doublet 240 is configured to correct for optical aberrations as introduced by the incorporation of surfaces required for the multi-bandpass filter coatings 205A, 205B. The illustrated achromatic doublet 240 includes two individual lenses, which can be made from glasses or other optical materials having different amounts of dispersion and different refractive indices. Other implementations may use three or more lenses. These achromatic doublet lenses can be designed to incorporate the multi-bandpass filter coatings 205A, 205B on the curved front surface 242 while eliminating optical aberrations introduced that would otherwise be present through the incorporation of a curved singlet optical surface with the deposited filter coatings 205A, 205B while still limiting optical or focusing power provided by the achromatic doublet 240 due to the combinatorial effect of the curved front surface 242 and the curved back surface of 244 while still keeping the primary elements for focusing light restricted to the lenses housed in housing 250. Thus, the achromatic doublet 240 can contribute to the high precision of image data captured by the system 200. These individual lenses can be mounted next to each other, for example being bonded or cemented together, and shaped such that the aberration of one of the lenses is counterbalanced by that of the other. The achromatic doublet 240 curved front surface 242 or the curved back surface 244 can be coated with the multi-bandpass filter coating 205A, 205B. Other doublet designs may be implemented with the systems described herein.

Figure 3C:
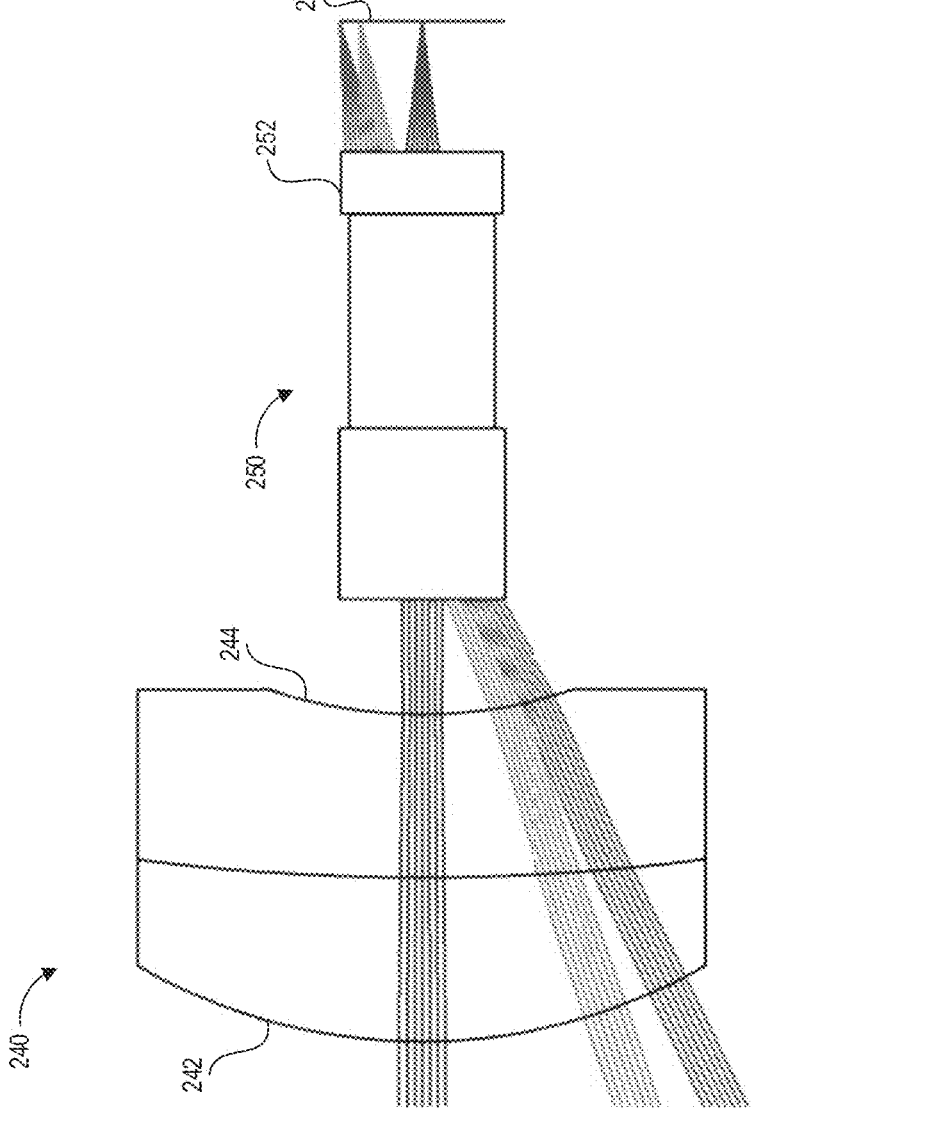
Figure 3D:
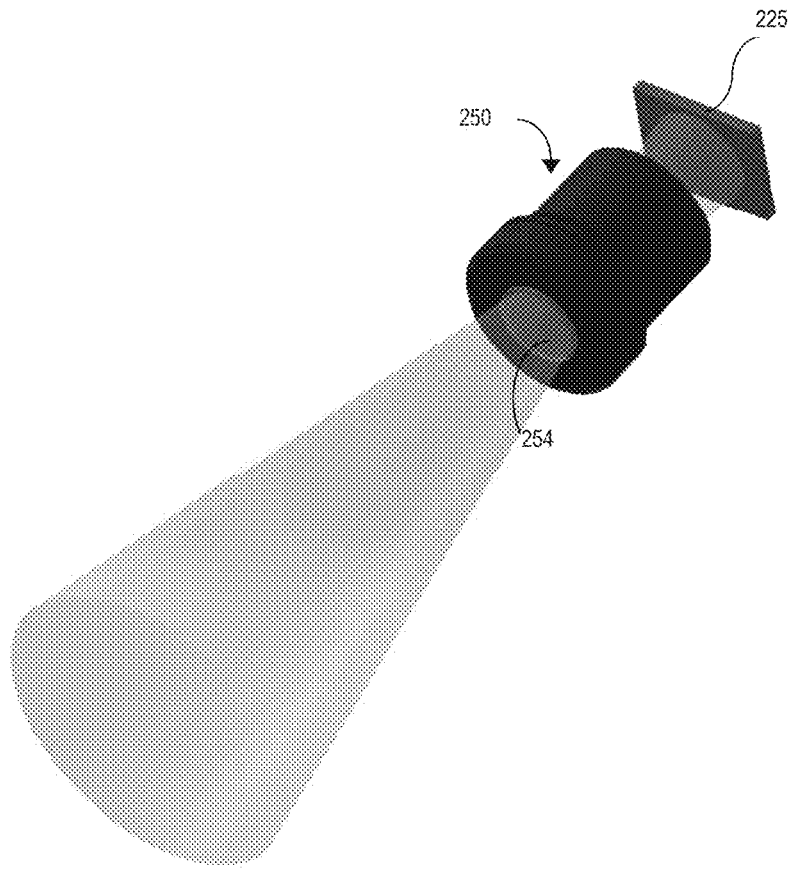

Further variations of the optical designs described herein may be implemented. For example, in some embodiments a light path may include a singlet or other optical singlet such as of the positive or negative meniscus variety as depicted in FIG. 3A instead of the doublet 240 depicted in FIG. 3B. FIG. 3C illustrates an example implementation in which a flat filter 252 is included between the lens housing 250 and the sensor 225. The achromatic doublet 240 in FIG. 3C provides optical aberration correction as introduced by the inclusion of the flat filter 252 containing a multi-bandpass transmission profile while not significantly contributing to the optical power as provided by the lenses contained in housing 250. FIG. 3D illustrates another example of an implementation in which the multi-bandpass coating is implemented by means of a multi-bandpass coating 254 applied to the front surface of the lens assembly contained within the housing 250. As such, this multi-bandpass coating 254 may be applied to any curved surface of any optical element residing within housing 250.

Single-Aperture Multispectral Imaging Systems and Methods

Figure 4:
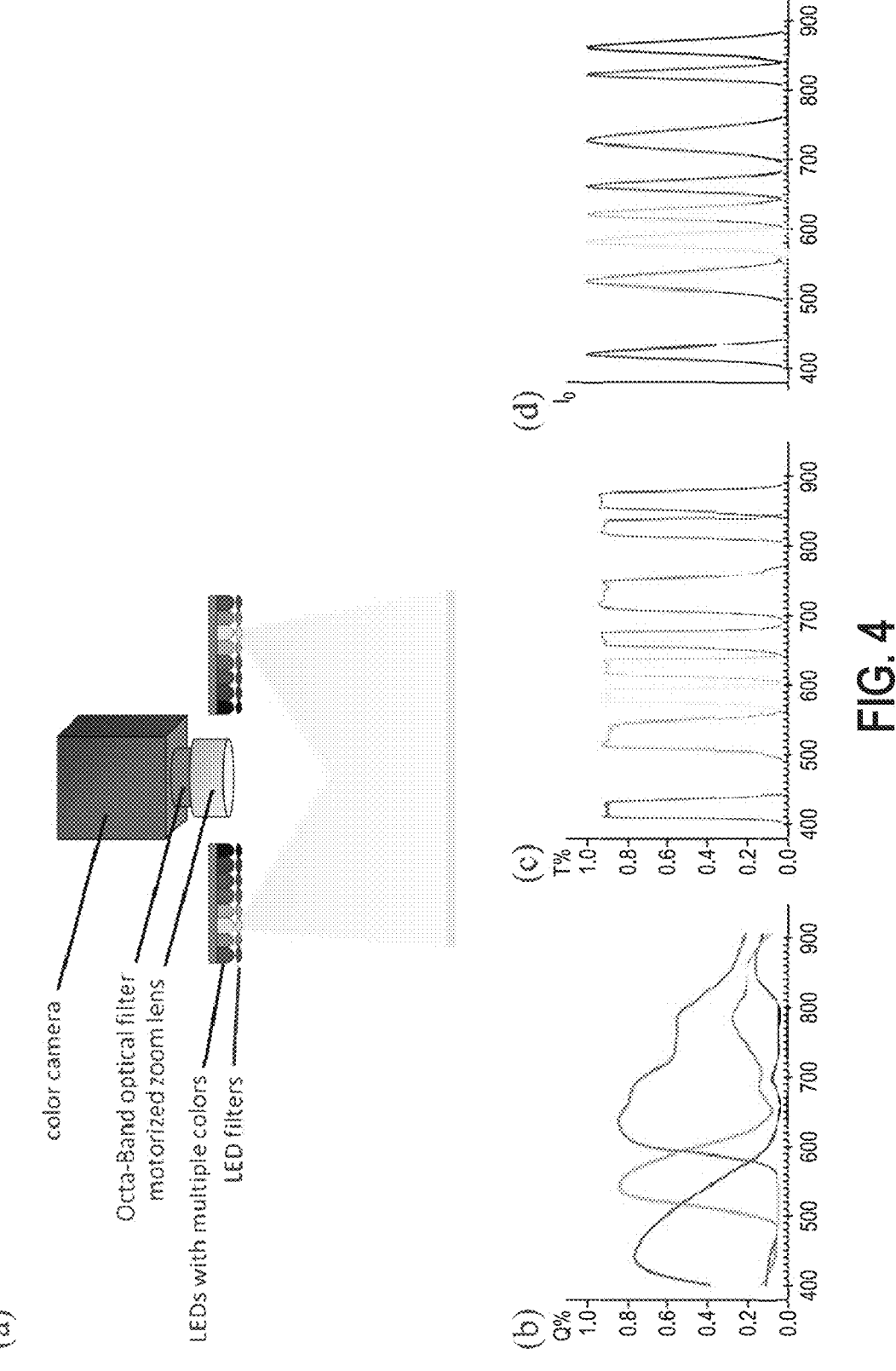
FIG. 4 schematically illustrates an example single-aperture multi-spectral imaging system in accordance with the present technology, including plots illustrating the performance of components thereof.

FIG. 4, at section (a), shows a system diagram of an example multispectral image system in accordance with the present disclosure. In this design, a color camera is the imaging sensor, although various other types of imaging sensors may be used in accordance with the present technology. A motorized zoom lens may also be included so the system is capable of capturing images with an adjustable field of view (FOV). A motorized zoom lens can advantageously enable adjustable FOVs for different imaging scenarios. For example, in biomedical applications for wound imaging, a large FOV may be desirable for imaging large-area burn wounds, while a small FOV may be desirable for imaging small-area features such as a diabetic foot ulcer (DFU) or other features. In one non-limiting example embodiment, a desirable FOV may range from 8 cm to 23 cm in diameter. An octa-band optical filter is placed in between the lens and camera where the bands are designed as the multi-spectral imaging bands. In this particular example, the central wavelengths of the 8 bands can be 420 nm, 525 nm, 581 nm, 620 nm, 660 nm, 726 nm, 820 nm, and 855 nm. 8 wavelengths of LED lights with the same spectral bands can be provided for illumination. In some embodiments, each LED band can selectively be turned on and off independently of the other LEDs. A band-pass optical filter is placed in front of each LED with a matched spectral band for spectral confinement of the illumination light from the LED.

FIG. 4, at section (b), shows the quantum efficiency (Q %) of RGB sensors in the camera. The blue, green, and red lines represent the blue, green, and red channels of the camera correspondingly. FIG. 4, at section (c), shows the transmission coefficient of the octa-band filter, where there are in total 8 bandpass bands over the spectrum. These 8 bands are the desired multispectral imaging bands. Correspondingly, FIG. 4, at section (d), shows the 8 independent LEDs' illumination intensities ($I_0$) over the spectrum. Their illumination bands can overlay with the octa-band filter bands.

Figure 5:
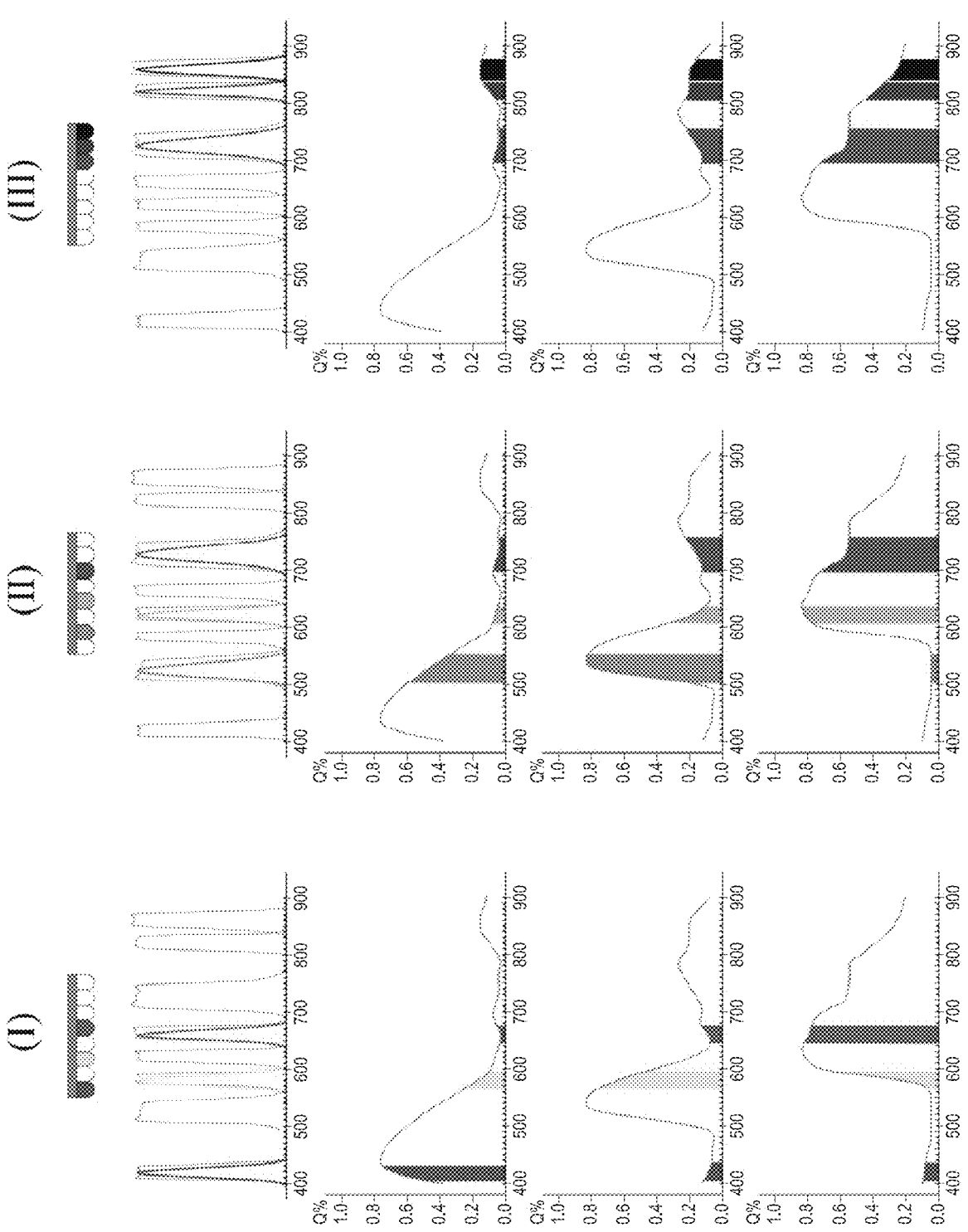
FIG. 5 illustrates an example time sequence of LED illumination in multi-spectral image acquisition and corresponding channel-specific sensing coefficients in accordance with the present technology.

FIG. 5 illustrates an example time sequence of LED illumination in MSI acquisition and the corresponding sensing coefficients in each channel, which may be implemented in conjunction with the multispectral image system of FIG. 4. The time sequence of FIG. 5 is merely exemplary as a demonstration of the illumination and spectral unmixing that may be utilized within the scope of the present technology. It will be understood that the system of FIG. 4 may be used in conjunction with different LED time sequences, and/or the time sequences of FIG. 5 may be used in conjunction with a different multispectral image system, without departing from the spirit or scope of the present technology.

First, in (I), LEDs channel 1, 3, and 5 (420 nm, 581 nm, and 660 nm) lights are turned on. During this time window, the camera acquires one image. The three wavelengths pass the optical filters and are captured by RGB channels in the camera, with different filter transmission coefficients (T %) and RGB sensing coefficients (Q %), as shown in (I). Second, as shown in (II), LEDs channel 1, 3, and 5 lights are turned off and channel 2, 4, and 6 (525 nm, 620 nm, and 726 nm) lights are turned on. Similarly, the camera acquires one image during this period and the three wavelengths are captured by the three camera channels with certain coefficients. Third, in (III), LED channel 2, 4 lights are turned off (while channel 6, 726 nm is still on) and channel 7, 8 lights (820 nm, 855 nm) are turned on, so that the camera acquires a third image about 6, 7, 8 wavelengths with certain coefficients.

In some embodiments, an initial calibration can be carried out. First, the camera acquires three images of a reference (e.g., a white zenith target or the like) in the following order: (1) when there is no LED illumination; (2) when LEDs channel 1, 3, and 5 (420 nm, 581 nm, and 660 nm) lights are turned on (all other LEDs channels are turned off); (3) When LEDs channel 2, 4, and 6 (525 nm, 620 nm, and 726 nm) lights are turned on (all other LEDs channels are turned off); (4) When LEDs channel 6, 7, and 8 (726 nm, 820 nm, and 855 nm) lights are turned on (all other LEDs channels are turned off). In some embodiments, the reference may be a white Zenith target that reflects ~95% of photons over the whole spectrum, which can be used for illumination flat field correction.

Next, the camera can acquire three images of an imaging target in the same sequences (e.g., no LED illumination, followed by channels 1, 3 and 5; channels 2, 4, and 6; and channels 6, 7, and 8). By background subtraction and flat field correction, the following expression can be used:

$$\text{Image} = I_0 \times R\% \times T\% \times Q\%$$

where $I_0$ is the bare illumination intensity, R % is the reflectance coefficients of the imaging target (which are unknown spectrums for calculation), T % is the transmission coefficients of the LED filters and the Octa-Band filter, and Q % is the quantum coefficients of the camera. Because the camera image has three channels (Blue, Green, Red) as three known values, and meanwhile the LED illuminations only contain three wavelengths at a time so that reflectance coefficients of three spectral bands (e.g., R % of channel 1, 3, 5) are the three unknown values to calculate at a time, it can solve the three unknown R % channels by an unmixing matrix, based on the follow matrix operation equation (using channel 1, 3, 5 as an example):

$$[R\%_{channel1} \quad R\%_{channel3} \quad R\%_{channel5}] \times$$

$$\begin{bmatrix} I_{0channel1} \times T\%_{channel1} \times Q\%_{Blue} & I_{0channel1} \times T\%_{channel1} \times Q\%_{Green} & I_{0channel1} \times T\%_{channel1} \times Q\%_{Red} \\ I_{0channel3} \times T\%_{channel3} \times Q\%_{Blue} & I_{0channel3} \times T\%_{channel3} \times Q\%_{Green} & I_{0channel3} \times T\%_{channel3} \times Q\%_{Red} \\ I_{0channel5} \times T\%_{channel5} \times Q\%_{Blue} & I_{0channel5} \times T\%_{channel5} \times Q\%_{Green} & I_{0channel5} \times T\%_{channel5} \times Q\%_{Red} \end{bmatrix} =$$

$$[\text{Image}_{Blue} \quad \text{Image}_{Green} \quad \text{Image}_{Red}]$$

where $[R\ \%_{channel1}\ R\ \%_{channel2}\ R\ \%_{channel3}]$ are three unknown values, [Image Blue, Image Green, Image Red] are three known values, and $[I_0 \times T\ \% \times Q\ \%]$ is the unmixing coefficients matrix. Thus, the reflectance coefficients are solved by:

$$[R\%_{channel1}\ R\%_{channel3}\ R\%_{channel5}] = [Image_{Blue}\ Image_{Green} Image_{Red}] \times$$

$$\begin{bmatrix} I_{0channel1} \times T\%_{channel1} \times Q\%_{Blue} & I_{0channel1} \times T\%_{channel1} \times Q\%_{Green} & I_{0channel1} \times T\%_{channel1} \times Q\%_{Red} \\ I_{0channel3} \times T\%_{channel3} \times Q\%_{Blue} & I_{0channel3} \times T\%_{channel3} \times Q\%_{Green} & I_{0channel3} \times T\%_{channel3} \times Q\%_{Red} \\ I_{0channel5} \times T\%_{channel5} \times Q\%_{Blue} & I_{0channel5} \times T\%_{channel5} \times Q\%_{Green} & I_{0channel5} \times T\%_{channel5} \times Q\%_{Red} \end{bmatrix}^{-1}$$

Similarly, the reflectance coefficients in all other channels 2, 4, 6, 7, 8 (525 nm, 620 nm, 726 nm, 820 nm, and 855 nm) are solved by corresponding unmixing matrices when LEDs illumination are turned on in particular wavelength combinations. Correspondingly, the 8 MSI images are generated based on the channel-specific images obtained via the three unmixing matrices.

The time sequences of image acquisition and the LEDs illumination combinations described above with reference to FIG. 5 is only one example way to acquire the 8 MSI images. In practice, the LED illumination and image acquisition time sequences can be designed with different combinations and/or timings, and a combination may be selected for use based on hardware performance, empirical results, etc. As an alternative, a monochrome camera can be used when each LED wavelength is designed to turn on individually so unmixing matrices are not required. In this case, performance can be evaluated by imaging a target and comparing the quality of MSI images with spectrum ground truth (i.e., color calibration).

Figure 6:
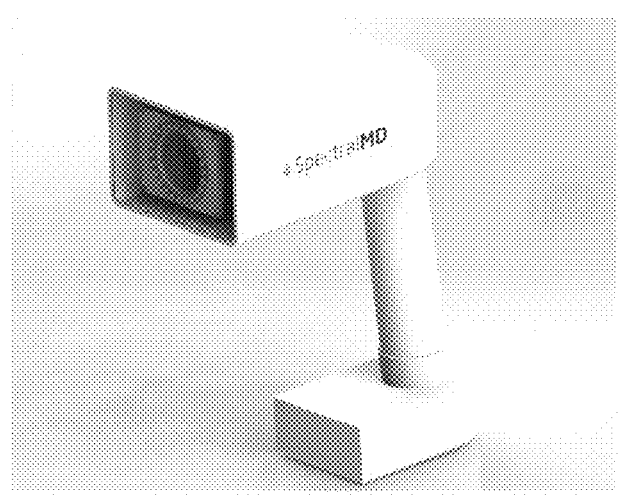
FIGS. 6 and 7 illustrate an example physical embodiment of a single-aperture multi-spectral imaging system in accordance with the present technology.
Figure 7:
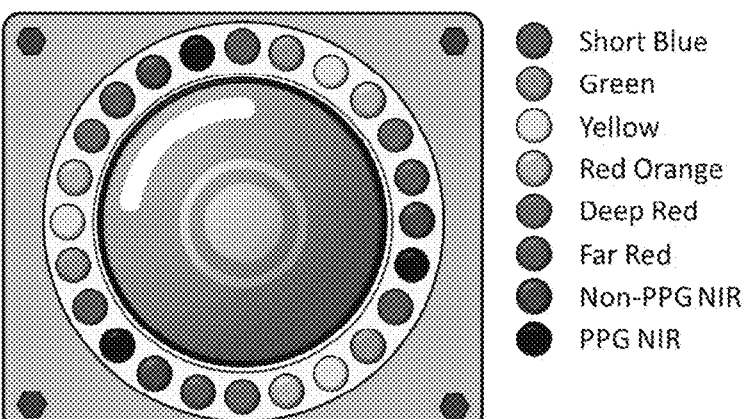

Example Implementations and Results of Single-Aperture Multispectral Imaging Systems FIGS. 6 and 7 illustrate an example physical embodiment of a single-aperture, single-camera multispectral image acquisition device which may be implemented in conjunction with the system and methods disclosed herein. FIG. 6 is a perspective view of a handheld device including a camera and an array of LEDs for providing multiplexed illumination as described above. One or more processors and memory for storing the acquired image data can be included within the handheld device of FIG. 6. Further processing of the image data, such as spectral unmixing as disclosed herein and/or generation of individual spectral images as further disclosed herein, may be performed within the handheld device of FIG. 6, or may be entirely or partially performed under control of one or more remote computing devices, alone or in conjunction with the device of FIG. 6, without departing from the scope of the present disclosure.

FIG. 7 illustrates an example LED configuration including a total of 24 LEDs, including 3 each of 8 different wavelength band LEDs, arranged in a circular configuration surrounding the single aperture of the image acquisition device. To reduce unmixing errors from complexity, the number of LED illumination colors are upgraded to 8 wavelengths, with each individually covers a pre-determined MSI spectral band whose central wavelengths may be around 420 nm, 525 nm, 581 nm, 620 nm, 660 nm, 726 nm, 820 nm, and 880 nm. Because of the single-aperture design of the imaging sensor, a new spatial arrangement of the LEDs has been developed so that the illumination board and the imaging sensor are in compacted into a smaller front-size. With a ring-shape design, it provides a desirable photo collection efficiency from the LED illumination to the camera aperture at the center. To ensure uniform illumination at a desired working distance (e.g., 40 cm in some embodiments), each LED color may carry up to 3 or more LED units on the illumination board, with each carrying 120° beam spread. A diffuser can be placed over the illumination board and spacers are specified to ensure that there would be sufficient distance between the LEDs and the diffuser to prevent thermal damage to the diffuser. Control of the individual LEDs can be accomplished using one or more processors integrated into the imaging head (e.g., the device of FIG. 6) so that different color combinations will be tested for an optimized image acquisition time sequence design. It also allows calibration-time tuning of illumination intensities of individual light sources for a high signal-to-noise ratio.

Figure 8:
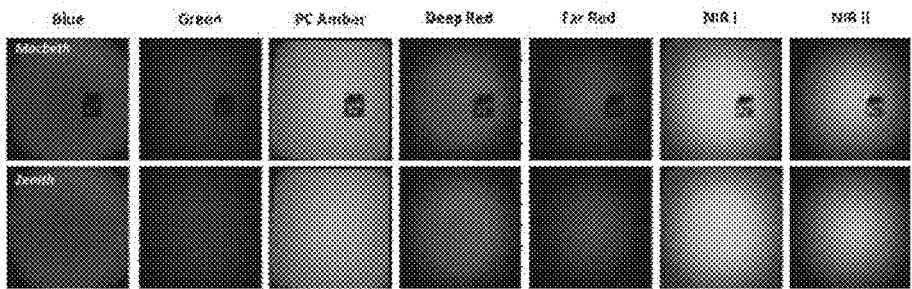
FIGS. 8-10 illustrate results of testing of a single-aperture system in accordance with the present technology.
Figure 9:
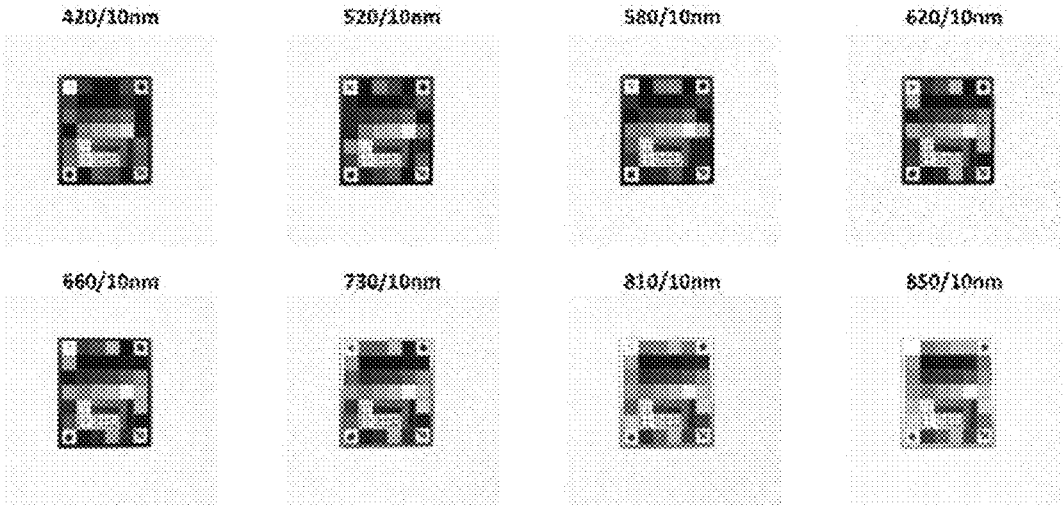
Figure 10:
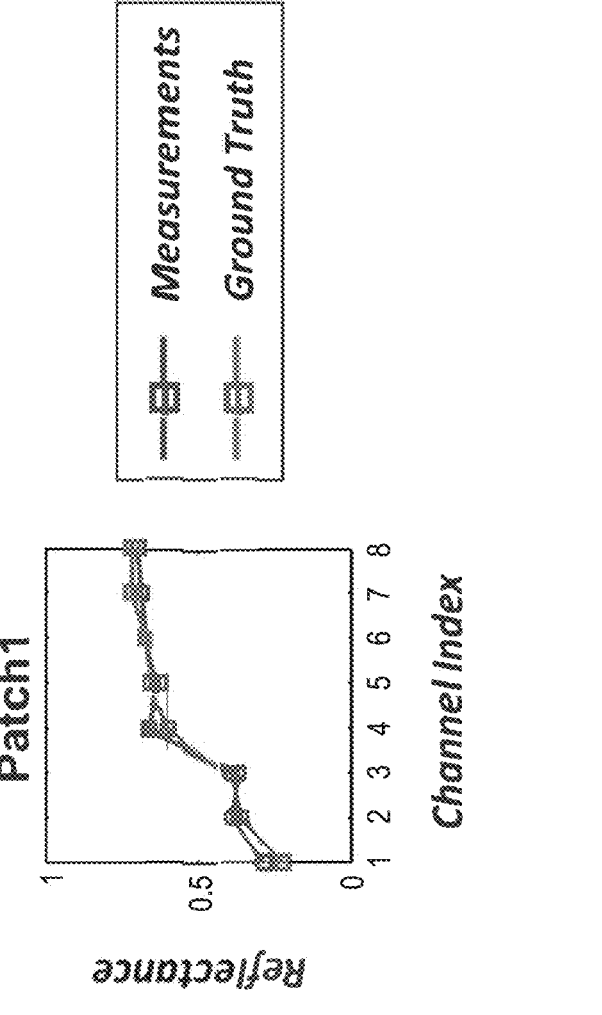
Figure 10:
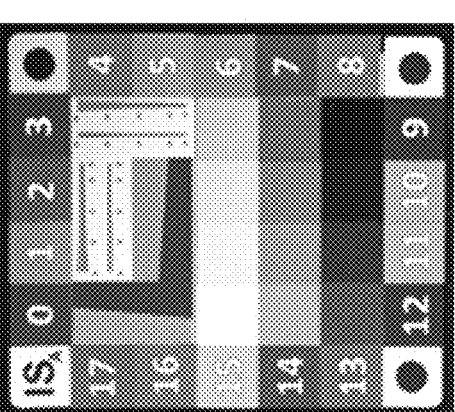
Figure 10:
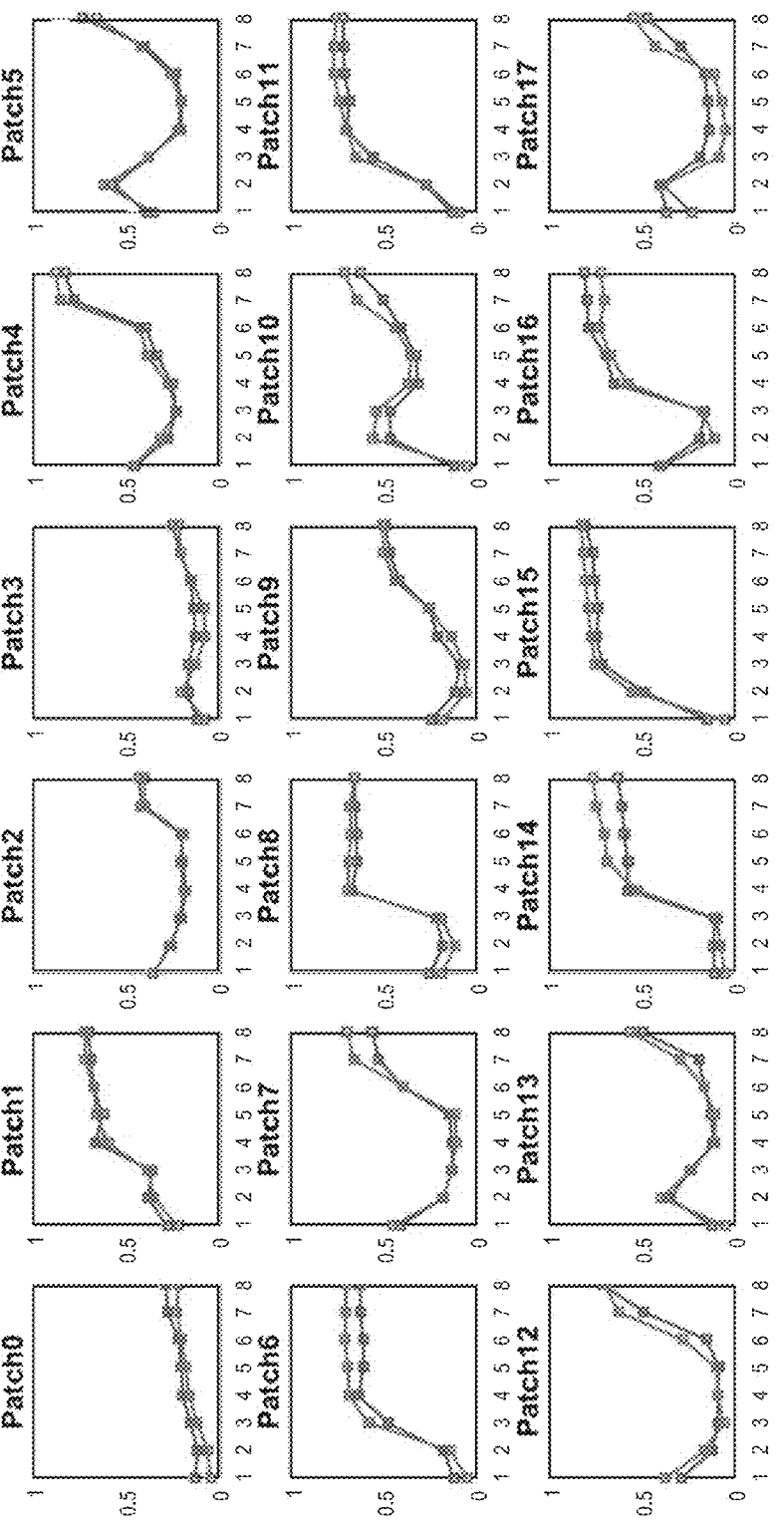

FIGS. 8-10 illustrate results of testing of a single-aperture system in accordance with the present technology. FIG. 8 depicts RGB images of both a Macbeth target and a Zenith target acquired from a single-lens, single-aperture, single-camera system under seven different color LED illumination conditions, with ambient room light subtracted as background. In this example trial, seven color LEDs (Blue, Green, PC Amber, Deep Red, Far Red, NIR I, NIR II) on an illumination board were turned on-and-off individually in a time sequence with a setting of 8 separate MSI bandpass optical filters (having central wavelength/full-width-half-maximum (FWHM): 420/10 nm, 520/10 nm, 580/10 nm, 620/10 nm, 660/10 nm, 730/10 nm, 810/10 nm, and 850/10 nm) so that a total 7×8=56 images were acquired on the RGB camera.

In a linear post-processing method, by summing up the 8 images acquired in 8 different filters when the same-color LED was illuminated, it equivalently represented having an octa-band filter with 7 RGB images acquired in 7 illumination conditions. A Macbeth target was imaged for spectral analysis and a 95%-reflectance Zenith target was imaged for flatfield correction. Then, 8 MSI images were generated through an unmixing algorithm. The unmixing principle is briefly described here. The detected signal (S) is an integration of multiplication of the illumination intensity (I), the target reflectance (R), the transmission coefficients of optics (T) including the lens and the bandpass filters and the quantum efficiency of the senor (Q) over the spectral band (λ):

$$\int(S_\lambda) = \int(I_\lambda \times R_\lambda \times T_\lambda \times Q_\lambda)$$

The target reflectance (R) is the measurement objective, and the detected signal (S) is the direct measurement. The octa-band filter confines optical transmission only in the 8 pre-determined MSI spectral windows so that there are only 8 unknown R measurements. By modulating 7 color LED illumination (I) with 3 spectral sensors whose quantum efficiency (Q) are identical (i.e., RGB channels), it provides a linear unmixing matrix with sufficient knowns (7×3=21) to solve the 8 unknowns. The 8 MSI images generated using this process are shown in FIG. 9.

After MSI images were generated, spectral accuracy was analyzed by comparing MSI spectrum of each patch on the Macbeth target to the ground truth obtained by a calibrated spectrometer. Results of the comparison are shown in FIG. 10. The comparison demonstrates a high spectral measurement accuracy (with an average correlation coefficient of 0.97) in the proposed upgrade to a single-aperture MSI system design.

Terminology

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

The disclosed processes may begin in response to an event, such as on a predetermined or dynamically determined schedule, on demand when initiated by a user or system administer, or in response to some other event. When the process is initiated, a set of executable program instructions stored on one or more non-transitory computer-readable media (e.g., hard drive, flash memory, removable media, etc.) may be loaded into memory (e.g., RAM) of a server or other computing device. The executable instructions may then be executed by a hardware-based computer processor of the computing device. In some embodiments, the process or portions thereof may be implemented on multiple computing devices and/or multiple processors, serially or in parallel.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multithreaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the scope of the disclosure. As can be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A multispectral image system comprising:
a light source configured to illuminate an object by selectively emitting light comprising one or more wavebands of a set of four or more predetermined wavebands;
an image sensor configured to receive a reflected portion of the emitted light that is reflected by the object;
an aperture positioned to allow the reflected portion of the emitted light to pass to the image sensor;
a multi-bandpass filter positioned over the aperture, wherein the multi-bandpass filter is configured to allow simultaneous passage of light in the four or more predetermined wavebands;
a memory storing instructions for generating and unmixing multispectral images; and
at least one processor configured by the instructions to at least:
cause the light source to emit light of a first subset of two or more of the predetermined wavebands at a first time;
receive, from the image sensor, first image data generated based on reflected light of the first subset;
cause the light source to emit light of a second subset of two or more of the predetermined wavebands at a second time different from the first time, wherein the second subset of two or more predetermined wavebands differs at least in part from the first subset of two or more predetermined wavebands;
receive, from the image sensor, second image data generated based on reflected light of the second subset;
process the first image data and the second image data to generate at least a first multispectral image and a second multispectral image; and
perform spectral unmixing to generate a plurality of single-waveband images of the object, each single-waveband image corresponding to one of the four or more predetermined wavebands.

2. The multispectral image system of claim 1, wherein the processor is further configured to:
cause the light source to emit light of a third or higher ordered subset of two or more of the predetermined wavebands; and
receive, from the image sensor, third or higher ordered image data generated based on reflected light of the third or higher ordered subset.

3. The multispectral image system of claim 1, wherein the light source comprises a plurality of light emitting diodes (LEDs), each LED configured to emit light at one of the four or more predetermined wavebands.

4. The multispectral image system of claim 3, wherein the at least one processor is further configured to control activation of individual LEDs of the light source to select the wavebands simultaneously emitted by the light source.

5. The multispectral image system of claim 4, wherein the processor controls activation of the individual LEDs by controlling an electronic switching shutter to selectively pass or block the light emitted by each individual LED.

6. The multispectral image system of claim 3, further comprising bandpass filters positioned over individual LEDs of the plurality of LEDs to provide precise spectral confinement of the light emitted by the individual LEDs.

7. The multispectral image system of claim 3, wherein the set of four or more predetermined wavebands comprises eight predetermined wavebands, and wherein the light source comprises eight LEDs, each LED configured to emit light at one of the predetermined wavebands.

8. The multispectral image system of claim 7, wherein the multi-bandpass filter comprises an octa-band filter configured to pass each of the eight predetermined wavebands.

9. The multispectral image system of claim 8, wherein the at least one processor is further configured by the instructions to cause the light source to emit light of a third subset of the predetermined wavebands and to receive, from the image sensor, third image data generated based on reflected light of the third subset.

10. The multispectral image system of claim 9, wherein the first, second, and third subsets each comprise three of the predetermined wavebands.

11. The multispectral image system of claim 7, wherein the predetermined wavebands are defined by central wavelengths ranging from ultraviolet (UV) to short wave infrared.

12. The multispectral image system of claim 11, wherein the predetermined wavebands have central wavelengths of 420 nm, 525 nm, 581 nm, 620 nm, 660 nm, 726 nm, 820 nm, and 855 nm, respectively.

13. The multispectral image system of claim 1, wherein the multi-bandpass filter comprises a plurality of wavebands that allow passage of light, each of the wavebands corresponding to one of the four or more predetermined wavebands.

14. The multispectral image system of claim 13, wherein the light source and the multi-bandpass filter comprise an equivalent number of wavebands, wherein each waveband in the light source aligns with a corresponding waveband in the multi-bandpass filter.

15. The multispectral image system of claim 1, further comprising a parfocal or varifocal zoom lens positioned over the aperture, the one or more processors further configured to control the parfocal or varifocal zoom lens to adjust a field of view (FOV) of the multispectral image system.

16. The multispectral image system of claim 15, wherein the parfocal or varifocal zoom lens is configured for automatic or manual adjustment of focus by changing a focal length (FL) of the lens.

17. The multispectral image system of claim 15, wherein adjusting the FOV of the multispectral image system does not affect an object distance between the object and the image sensor.

18. The multispectral image sensor of claim 15, wherein the one or more processors are further configured to adjust the FOV of the multispectral image system by changing an object distance between the object and the image sensor.

19. The multispectral image sensor of claim 18, wherein the processor is further configured to compensate for contrast lost through the zoom lens.

20. The multispectral image system of claim 15, wherein the FOV is adjustable over at least a range of 8 cm to 23 cm.

21. The multispectral image system of claim 20, wherein the system retains high spatial resolution by without reducing sampling numbers in the FOV, which is different from a digital cropping method by post-processing where resolution is sacrificed.

22. The multispectral image system of claim 1, wherein the one or more processors are further configured to generate a natural pseudocolor visualization of the object based on the multispectral images.

23. The multispectral image system of claim 1, wherein the one or more processors are configured to perform the spectral unmixing by solving for reflectance coefficients of the object using a matrix operation equation.

24. The multispectral image system of claim 23, wherein the reflectance coefficients are determined based at least in part on channel-specific values of bare illumination intensity, transmission coefficients of the multi-bandpass filter, and quantum coefficients of the image sensor.

25. The multispectral image system of claim 1, wherein the multispectral image system is capable of capturing three or more multispectral images in less than 100 milliseconds.

26. The multispectral image system of claim 1, wherein the object is a tissue region.

27. The multispectral image system of claim 26, wherein the tissue comprises a wound, a cancer, an ulcer, or a burn.

28. The multispectral image system of claim 27, wherein the wound comprises a diabetic ulcer, a non-diabetic ulcer, a chronic ulcer, a post-surgical incision, an amputation site, a burn, a cancerous lesion, or damaged tissue.

29. The multispectral image system of claim 26 for use in identifying a tissue classification such as living or healthy tissue, dead or necrotic tissue, perfused tissue or non-perfused tissue, ischemic or non-ischemic tissue or for use in identifying a healing score of a tissue, such as a proclivity to heal by at least 50% after 30 days with standard of care therapy or a proclivity to not heal by at least 50% after 30 days with standard of care therapy.

30. The multispectral image system of claim 26 for use in imaging a wound, a cancer, an ulcer, or a burn, such as a diabetic ulcer, a non-diabetic ulcer, a chronic ulcer, a post-surgical incision, an amputation site, a burn, a cancerous lesion, or damaged tissue.

* * * * *